United States Patent
Harris

(10) Patent No.: US 12,307,822 B1
(45) Date of Patent: May 20, 2025

(54) SYSTEMS AND METHODS FOR FACIAL IMAGING PROCESSING TO IDENTIFY FACIAL MOVEMENTS AND GENERATE USER-SPECIFIC ANALYTICS AND RECOMMENDATIONS THEREFROM

(71) Applicant: Jawzrsize, LLC, Wailuku, HI (US)

(72) Inventor: Brandon Harris, St. Petersburg, FL (US)

(73) Assignee: Jawzrsize, LLC, Wailuku, HI (US)

( * ) Notice: Subject to any disclaimer, the term of this patent is extended or adjusted under 35 U.S.C. 154(b) by 0 days.

(21) Appl. No.: 18/737,300

(22) Filed: Jun. 7, 2024

(51) Int. Cl.
*G06V 40/16* (2022.01)
*G06T 7/00* (2017.01)
*G06V 40/20* (2022.01)
*G16H 20/30* (2018.01)

(52) U.S. Cl.
CPC ............ *G06V 40/20* (2022.01); *G06T 7/0012* (2013.01); *G06V 40/16* (2022.01); *G16H 20/30* (2018.01); *G06T 2207/30201* (2013.01)

(58) Field of Classification Search
CPC ...... G06V 40/20; G06V 40/16; G06T 7/0012; G06T 2207/30201; G16H 20/30
See application file for complete search history.

(56) References Cited

U.S. PATENT DOCUMENTS

2024/0212820 A1* 6/2024 Kim .................. A63B 71/0619

FOREIGN PATENT DOCUMENTS

KR 2022123493 A * 9/2022

OTHER PUBLICATIONS

Schätz et al. "Face Movement Analysis with MS Kinect." International Workshop on Computational Intelligence for Multimedia Understanding (IWCIM), DOI: 10.1109/IWCIM.2016.7801179, Oct. 27, 2016, 5 pages (Year: 2016).*

* cited by examiner

*Primary Examiner* — Jon Chang
(74) *Attorney, Agent, or Firm* — Thomas | Horstemeyer, LLP

(57) ABSTRACT

In general, various aspects of the present invention provide methods, apparatuses, systems, computing devices, computing entities, and/or the like for generating user-specific analytics from facial imaging data. In various aspects, a method is provided that comprises: receiving facial imaging data of a user; accessing user attribute data for the user; processing the facial imaging data and the user attribute data using at least one of a rules-based model or a machine learning model to generate a user-specific first data analytic for the user; generating a graphical user interface comprising an indication of the first data analytic; and providing the graphical user interface for display on a computing device.

17 Claims, 18 Drawing Sheets

SYSTEMS AND METHODS FOR FACIAL IMAGING PROCESSING TO IDENTIFY FACIAL MOVEMENTS AND GENERATE USER-SPECIFIC ANALYTICS AND RECOMMENDATIONS THEREFROM

TECHNICAL FIELD

The present disclosure relates generally to data processing systems for processing facial imaging data using at least one of a rules-based model or a machine learning model to identify facial movements for determining user-specific analytics.

BACKGROUND

A technical challenge related to analyzing facial images includes accurately identifying, from the facial imaging data, a type and quantity of facial movements that an individual has performed. Furthermore, there are technical challenges related to diagnosing facial defects from facial imaging data, generating movement plans for improving the facial defects, confirming that the plans are being followed, and tracking defect correction progress. As such, there is a need for improved systems and methods for identifying facial movements from facial imaging data, and generating user-specific analytics and recommendations.

SUMMARY

In general, various aspects of the present disclosure provide methods, apparatuses, systems, computing devices, computing entities, and/or the like for generating user-specific analytics from facial imaging data. In accordance with various aspects, a method is provided. Accordingly, the method includes a computer-implemented data processing method of generating user-specific analytics from facial imaging data, comprising: (1) receiving, by computing hardware, facial imaging data of a user, the facial imaging data including imaging data of at least a portion of a jaw and facial structure of the user; (2) accessing, by the computing hardware, user attribute data for the user, the user attribute data defining one or more of: (A) an age of the user; (B) a gender of the user; (C) a weight of the user; (D) a face shape of the user; or (E) a relative position of one or more user facial features; (3) processing, by the computing hardware, the facial imaging data and the user attribute data using at least one of a rules-based model or a machine learning model to generate a user-specific first data analytic for the user, the first data analytic comprising at least one of: (A) a number of calories burned by the user during a time period demonstrated by the facial imaging data; or (B) a number of repetitions of a particular movement performed by at least one of the at least a portion of the jaw or the facial structure of the user; and (4) generating, by the computing hardware, a graphical user interface comprising an indication of the first data analytic; and (5) providing, by the computing hardware, the graphical user interface for display on a computing device.

In some aspects, the method further comprise: (1) analyzing, by the computing hardware, the facial imaging data; (2) determining, based on analysis of the facial imaging data, that the user has a jaw exercise apparatus in a mouth of the user; (3) determining, by the computing hardware, a type of the jaw exercise device; and (4) modifying, by the computing hardware, the first data analytic based at least in part on the type of the jaw exercise device. In particular embodiments, the first data analytic comprises the number of repetitions of the particular movement; and the method further comprises providing, by the computing hardware for each repetition of the repetitions of the particular movement, a particular input to the computing device. In some aspects, the method further comprise: (1) analyzing, by the computing hardware, the facial imaging data to identify at least one facial defect; (2) receiving, by the computing hardware, second facial imaging data; (3) analyzing, by the computing hardware, the second facial imaging data to determine a change in the at least one facial defect; and (4) processing, by the computing hardware, the facial imaging data, the at least one facial defect, and the change in the at least one facial defect to determine a correction progress of the at least one facial defect; and (5) providing, by the computing hardware, an indication of the correction progress of the at least one facial defect for display on a user interface.

In some aspects, the method further comprises: (1) processing, by the computing hardware, the facial imaging data, the user attribute data, and the at least one facial defect using at least one of a rules-based model or a machine learning model to generate a user-specific defect correction plan; and (2) generating, by the user interface, a user interface comprising the user-specific defect correction plan. In various embodiments, the at least one of the rules-based model or the machine learning model were trained with historical facial progress data and facial movement data for each user in a set of users.

A system, in various embodiments, comprises: (1) a non-transitory computer-readable medium storing instructions; and (2) a processing device communicatively coupled to the non-transitory computer-readable medium. In particular embodiment, the processing device is configured to execute the instructions and thereby perform operations comprising: (1) receiving facial imaging data of a user, the facial imaging data including imaging data of at least a portion of a jaw and facial structure of the user; (2) accessing user attribute data for the user, the user attribute data defining one or more of: (A) an age of the user; (B) a gender of the user; (C) a weight of the user; (D) a face shape of the user; or (E) a relative position of one or more user facial features; (3) processing the facial imaging data and the user attribute data using at least one of a rules-based model or a machine learning model to generate a user-specific first data analytic for the user, the first data analytic comprising at least one of: (A) a number of calories burned by the user during a time period demonstrated by the facial imaging data; or (B) a number of repetitions of a particular movement performed by at least one of the at least a portion of the jaw or the facial structure of the user; (4) generating a graphical user interface comprising an indication of the first data analytic; and (5) providing the graphical user interface for display on a computing device.

In some aspects, the operations further comprise: (1) analyzing the facial imaging data; (2) determining that the user has a jaw exercise apparatus in a mouth of the user; (3) determining a type of the jaw exercise device; and (4) modifying the first data analytic based at least in part on the type of the jaw exercise device. In some embodiments, the first data analytic comprises the number of repetitions of the particular movement; and the operations further comprise providing, for each repetition of the repetitions of the particular movement, a particular input to the computing device. In various aspects, the operations further comprise: (1) analyzing the facial imaging data to identify at least one facial defect; (2) receiving second facial imaging data; (3) analyzing the second facial imaging data to determine a change in the at least one facial defect; (4) processing the facial imaging data, the at least one facial defect, and the change in the at least one facial defect to determine a correction progress of the at least one facial defect; and (5) providing an indication of the correction progress of the at least one facial defect for display on a user interface.

In still other embodiments, the operations further comprise: (1) processing the facial imaging data, the user attribute data, and the at least one facial defect using at least one of a rules-based model or a machine learning model to generate a user-specific defect correction plan; and (2) generating a user interface comprising the user-specific defect correction plan.

In particular embodiments, the at least one of the rules-based model or the machine learning model were trained with historical facial progress data and facial movement data for each user in a set of users. In some aspects, the operations further comprise: (1) analyzing the facial imaging data to identify at least one facial defect; (2) processing the facial imaging data, the user attribute data, and the at least one facial defect using at least one of a rules-based model or a machine learning model to generate a user-specific defect correction plan; and (3) generating a user interface comprising the user-specific defect correction plan.

A non-transitory computer-readable medium, in various embodiments, has program code that is stored thereon. In some embodiments, the program code executable by one or more processing devices for performing operations comprising: (1) receiving facial imaging data of a user, the facial imaging data including imaging data of at least a portion of a jaw and facial structure of the user; (2) accessing user attribute data for the user; (3) processing the facial imaging data and the user attribute data using at least one of a rules-based model or a machine learning model to generate a user-specific first data analytic for the user, the first data analytic comprising at least one of: (A) a number of calories burned by the user during a time period demonstrated by the facial imaging data; or (B) a number of repetitions of a particular movement performed by at least one of the at least a portion of the jaw or the facial structure of the user; (4) generating a graphical user interface comprising an indication of the first data analytic; and (5) providing the graphical user interface for display on a computing device.

In some embodiments, the operations further comprises: (1) analyzing the facial imaging data; (2) determining that the user has a jaw exercise apparatus in a mouth of the user; (3) determining a type of the jaw exercise device; and (4) modifying the first data analytic based at least in part on the type of the jaw exercise device. In particular embodiments, the first data analytic comprises the number of repetitions of the particular movement; and the operations further comprise providing, for each repetition of the repetitions of the particular movement, a particular input to the computing device.

In a particular aspects, the operations further comprise: (1) analyzing the facial imaging data to identify at least one facial defect; (2) receiving second facial imaging data; (3) analyzing the second facial imaging data to determine a change in the at least one facial defect; (4) processing the facial imaging data, the at least one facial defect, and the change in the at least one facial defect to determine a correction progress of the at least one facial defect; and (5) providing an indication of the correction progress of the at least one facial defect for display on a user interface. In still other aspects, the operations further comprise: (1) processing the facial imaging data, the user attribute data, and the at least one facial defect using at least one of a rules-based model or a machine learning model to generate a user-specific defect correction plan; and (2) generating a user interface comprising the user-specific defect correction plan.

In some embodiments, the at least one of the rules-based model or the machine learning model were trained with historical facial progress data and facial movement data for each user in a set of users. In other embodiments, the operations further comprise: (1) analyzing the facial imaging data to identify at least one facial defect; (2) processing the facial imaging data, the user attribute data, and the at least one facial defect using at least one of a rules-based model or a machine learning model to generate a user-specific defect correction plan; and (3) generating a user interface comprising the user-specific defect correction plan.

BRIEF DESCRIPTION OF THE DRAWINGS

In the course of this description, reference will be made to the accompanying drawings, which are not necessarily drawn to scale, and wherein.

DETAILED DESCRIPTION

Various embodiments of the disclosure now will be described more fully hereinafter with reference to the accompanying drawings. It should be understood that the disclosure may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Overview

As noted, a technical challenge related to analyzing facial images includes accurately identifying, from the facial imaging data, a type and quantity of facial movements that an individual has performed. For example, an individual desiring to physically train their head, neck, face, jaw, or other portion thereof may perform specific movements that target specific muscular or skeletal aspects of those portions of the body. When performing such specific movements, a user may desire to accurately track their form (i.e., to ensure that they are performing a particular movement targeting a particular portion of their face, head or neck in the appropriate manner) in addition to the quantity of repetitions of a specific movement and other factors. In various aspects, determining such data from facial imaging data (e.g., still images or video images) of an individual can be technically challenging. In particular, each user may have a differently shaped face, may be performing different motions, may utilize (or not utilize) one or more mouthpieces during the course of the movements, etc. In addition, the subtlety of facial movement required for certain movements (the face has dozens of individual muscles-compare this to other major muscle groups such as the chest, biceps, etc.) may render such movements technically difficult to identify from facial imaging data (in comparison to larger range of motion movements such as a squat or curling motion).

As such, various aspects of a facial image processing and analysis computing system described herein provide improvements to facial image processing by automatically applying various rules of a particular type to control the manner in which computing devices dynamically determine that particular movements have occurred, and the impact of such movements. This may, for example, result in a user-specific determination of movement impact through tracking an individual user's progress across a set of movement sessions and during an individual movement session. Additionally, certain aspects automatically apply customized sets of rules to determine movement impact in the form of calories burned and other factors.

Example Computing Environment

Figure 1:
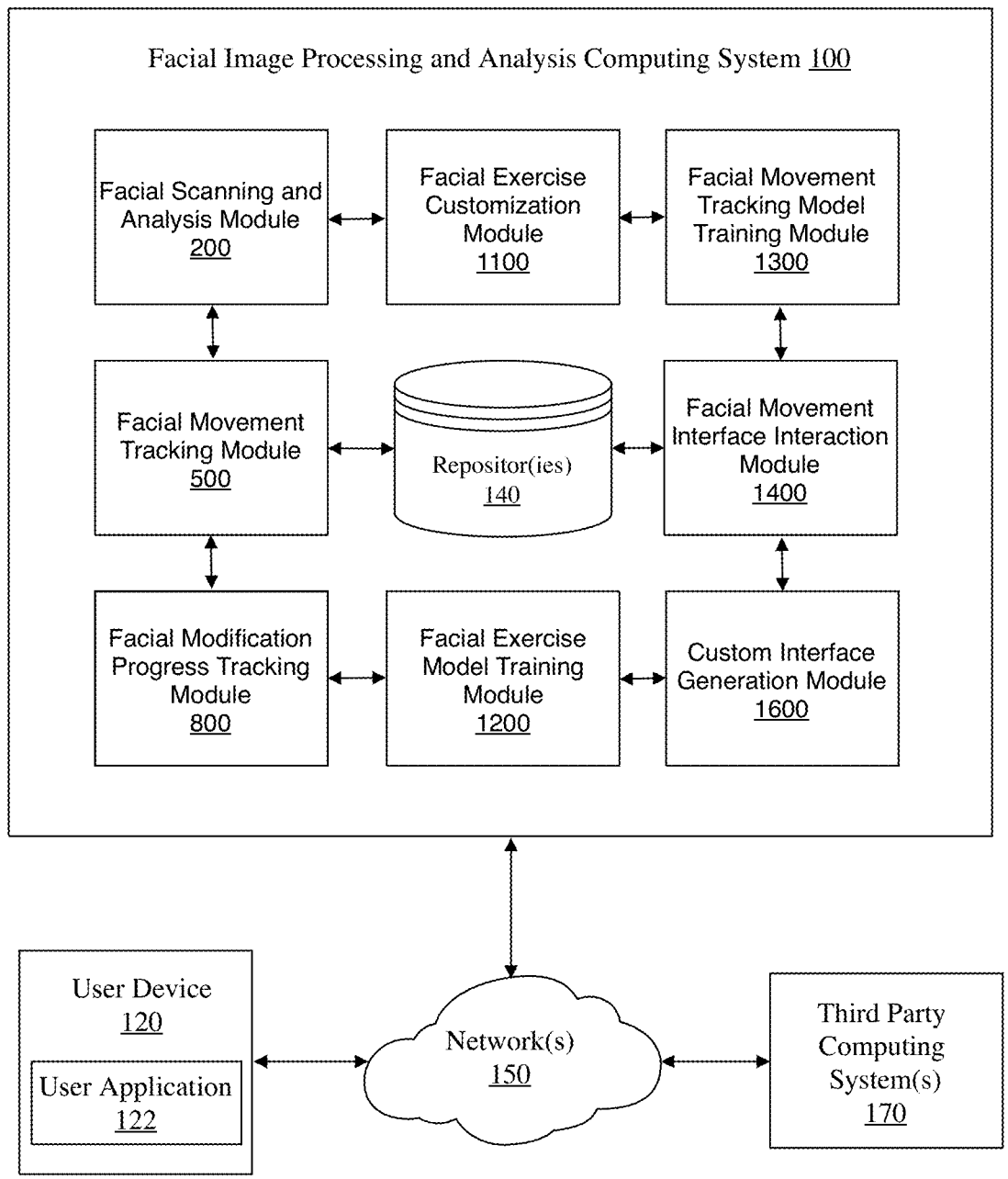
FIG. 1 depicts an example of a computing environment that can be used for processing and analyzing facial imaging data to derive particular metrics therefrom in accordance with various aspects.

FIG. 1 depicts an example of a computing environment that can be used for processing and analyzing facial imaging data to derive particular metrics therefrom. For example, users may be interested in platforms that accurately assess facial movements from imaging data in order to provide accurate, consistent data for use in tracking user progress against themselves and other users.

In various aspects, a facial image processing and analysis computing system 100 is provided within the computing environment that includes software components and/or hardware components to aid users in capturing facial imaging data and analyzing the data to determine desired analytics. For instance, the facial image processing and analysis computing system 100 may provide a facial imaging platform or other service that is accessible over one or more networks 150 (e.g., the Internet) by a user accessing a user application 122 on a user computing device 120.

Here, the facial image processing and analysis computing system 100 may provide the user computing device 120 with one or more graphical user interfaces (e.g., webpages, software applications, etc.) through the service to access the facial image processing and analysis computing system 100. The user may use the service in performing functionality associated with capturing facial image data, analyzing the facial imaging data to track particular facial movements, and generating analytics related to the movement data that are specific to the user. For example, the facial image processing and analysis computing system 100 may provide customized user interfaces that include data relevant to the user derived from facial image analyses. In this way, the facial image processing and analysis computing system 100 may provide graphical user interfaces that are more useful to each individual user and that also facilitate the tracking and progression of facial movements and defect correction in a more streamlined manner than conventional systems.

In addition to the graphical user interfaces, the facial image processing and analysis computing system 100 may include one or more interfaces (e.g., application programming interfaces (APIs)) for communicating and/or accessing the third party computing system(s) 170 over the network(s) 150. For instance, the facial image processing and analysis computing system 100 may access a third party computing system 170 via one of the interfaces to access user data, sensor data, or third party computing component data for providing more accurately generated analytics (i.e., that are more specific to the user). For example, the facial image processing and analysis computing system 100 may access a third party computing system 170 that stores heart rate data, meal data, or other user-specific data that may modify a determination of data resulting from particularly identified facial movements.

In some instances, the facial image processing and analysis computing system 100 may include one or more repositories 140 that can be used for storing data related to the user, to particular data analysis results, etc., In other aspects, the one or more repositories 140 may store data related to facial exercise training plans, or other suitable data.

In some aspects, the facial image processing and analysis computing system 100 executes a Facial Scanning and Analysis Module 200 to scan and analyze facial imaging data. The Facial Scanning and Analysis Module 200 may be configured to identify facial defects based on the facial imaging data analysis.

In some aspects, the facial image processing and analysis computing system 100 executes Facial Movement Tracking Module 500 for tracking facial movements of an individual in accordance with various aspects of the present disclosure. The Facial Movement Tracking Module 500 may be configured to identify completion of particular movements by the individual (i.e., facial movements, jam movements, etc.) from the facial imaging data.

In additional or alternative aspects, the facial image processing and analysis computing system 100 executes Facial modification Progress Tracking Module 800 for process for tracking facial modification progress. The Facial Modification Progress Tracking Module 800 may, for example, track user progress toward correcting one or more identified facial defects, toward one or more goals, etc.

In additional or alternative aspects, the facial image processing and analysis computing system 100 executes a Facial Exercise Customization Module 1100 for generating a user-specific customized facial exercise plan. The Facial Exercise Customization Module 1100 may, for example, be configured to generate the user-specific customized facial exercise plan to include a set of exercises for: (1) correcting one or more identified facial defects; (2) meeting one or more user-provided goals; etc.

In additional or alternative aspects, the facial image processing and analysis computing system 100 executes a Facial Exercise Model Training Module 1200 for providing training data to train a machine learning model for generating customized facial exercise/movement plans. The training data may include, for example, progress data in conjunction with tracked facial movement data for a set of users.

In additional or alternative aspects, facial image processing and analysis computing system 100 executes Facial Movement Tracking Model Training Module 1300 for providing training data to train a machine learning model for tracking facial movement. In some aspects, the Facial Movement Tracking Model Training Module 1300 provides the training data that includes tracked facial movements and user confirmation thereof, markers of particular movements, and other movement data.

In additional or alternative aspects, the facial image processing and analysis computing system 100 executes a Facial Movement Interface Interaction Module 1400 for modifying a user interface based on identified facial movements. In some aspects, the Facial Movement Interface Interaction Module 1400 may enable the user to utilize facial movements (i.e., identified by the system) as input for a computing device.

In additional or alternative aspects, the facial image processing and analysis computing system 100 executes Custom Interface Generation Module 1600 for generating customized user interfaces.

Further detail is provided below regarding the configuration and functionality of the Facial Scanning and Analysis Module 200, the Facial Movement Tracking Module 500, the Facial Modification Progress Tracking Module 800, the Facial Exercise Customization Module 1100, the Facial Exercise Model Training Module 1200, the Facial Movement Tracking Model Training Module 1300, The Facial Movement Interface Interaction Module 1400, and the Custom Interface Generation Module 1600, according to various aspects of the disclosure.

The number of devices depicted in FIG. 1 are provided for illustrative purposes. In some aspects, different number of devices may be used. In various aspects, for example, while certain devices or systems are shown as single devices in FIG. 1, multiple devices may instead be used to implement these devices or systems.

In some aspects, the facial image processing and analysis computing system 100 can include one or more third-party devices such as, for example, one or more servers operating in a distributed manner. The facial image processing and analysis computing system 100 can include any computing device or group of computing devices, and/or one or more server devices.

Although the data repository 140 is shown as a single component, these components 140 may include, in other aspects, a single server and/or repository, servers and/or repositories, one or more cloud-based servers and/or repositories, or any other suitable configuration.

Facial Scanning and Analysis Module

Figure 2:
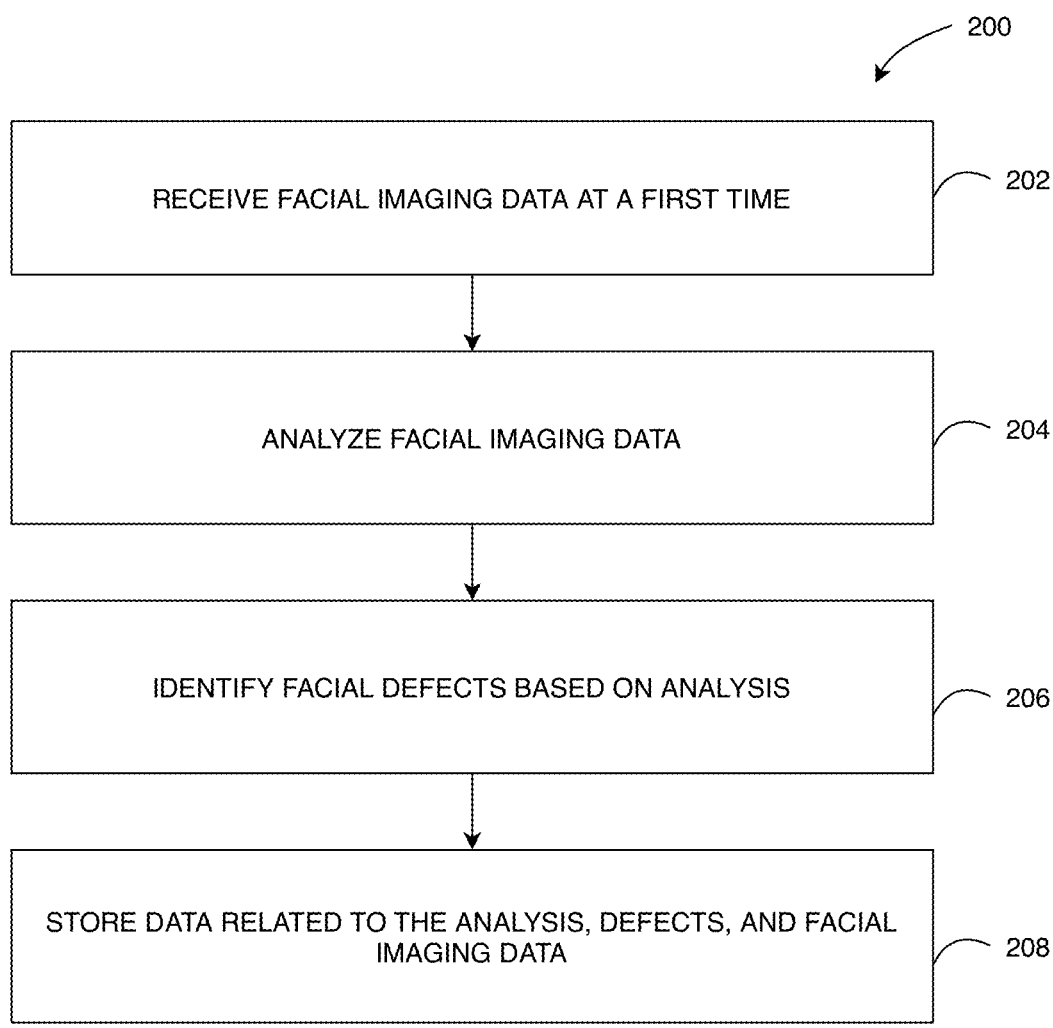
FIG. 2 depicts an example of a process for scanning and analyzing facial imaging data in accordance with various aspects of the present disclosure.

Turning now to FIG. 2, additional details are provided regarding a Facial Scanning and Analysis Module 200. For instance, the flow diagram shown in FIG. 2 may correspond to operations executed by computing hardware found in facial image processing and analysis computing system 100 as it executes the Facial Scanning and Analysis Module 200.

In some aspects, the facial image processing and analysis computing system 100, when executing steps related to the Facial Scanning and Analysis Module 200, provides a software application 122 to a user device 120 and provides user interfaces for capturing one or more facial images (e.g., video, one or more still images, etc.). For example, the facial image processing and analysis computing system 100 may provide the facial imaging capture interface as a website accessible over a network 150 by a user via a client application 122, such as a browser application, executing on a user device 120. In another example, the facial image processing and analysis computing system 100 may provide the facial image capture interface(s) and/or application through the client application 122 executing on the user device 120 in which the client application 122 may be a proprietary software application installed on the user device 120.

At operation 202, the Facial Scanning and Analysis Module 200 receives facial imaging data at a first time. In various aspects, the Facial Scanning and Analysis Module 200 is configured to receive the facial imaging data in any suitable manner, such as via the software application 122 executing on a user device 120 (e.g., via a network 150). In particular aspects, the facial imaging data includes initial facial imaging data for a user initiating a new movement program (e.g., exercise program). The Facial Scanning and Analysis Module 200 may receive the facial imaging data directly vie a client application 122 for capturing facial images. The imaging data may include, for example, video, still images, etc. In various aspects, the imaging data includes at least a portion of a face of an individual.

Figure 3:
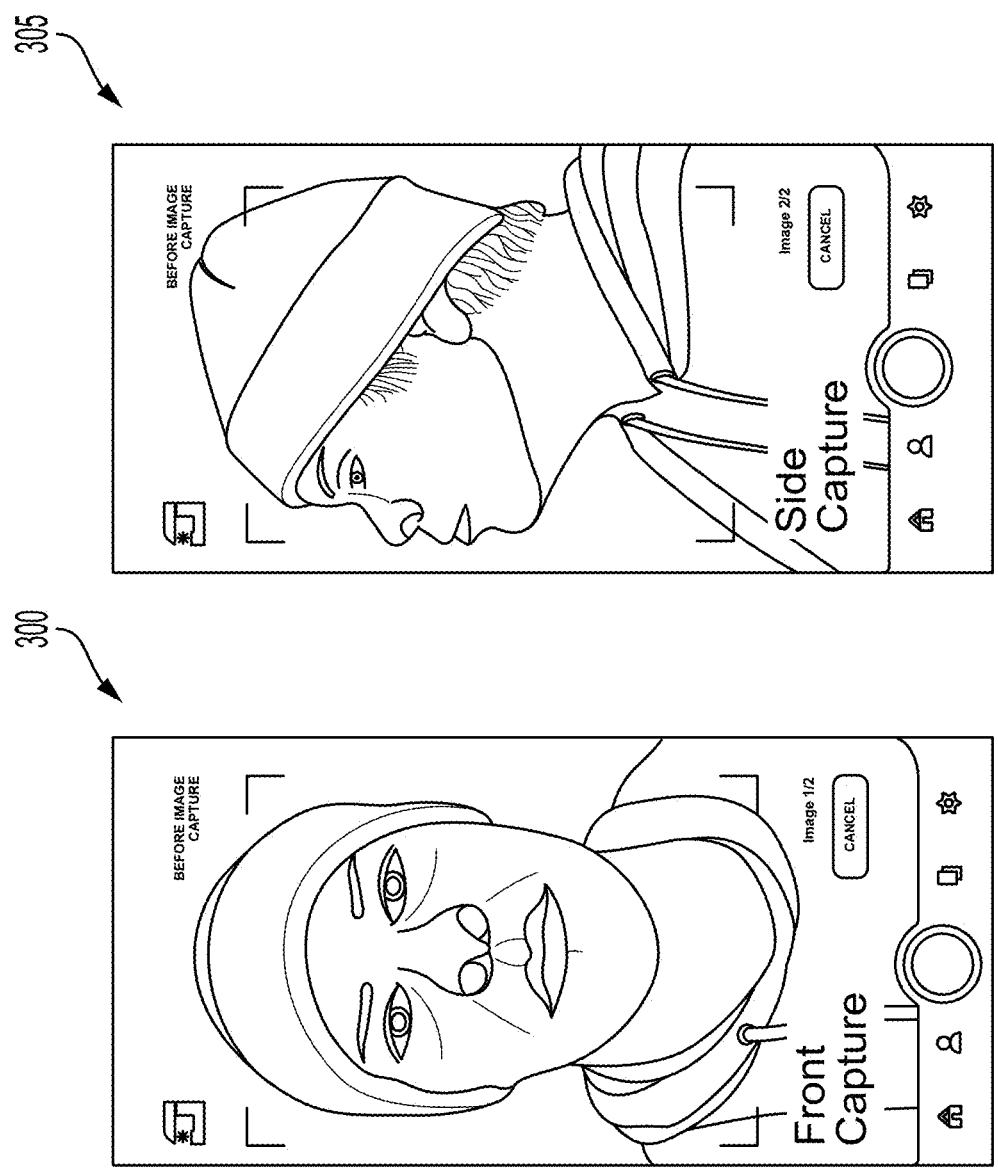
FIG. 3 depicts an example of a facial imaging data capture interface in accordance with various aspects of the present disclosure.

FIG. 3 depicts an exemplary image capture interface via which the system may receive facial imaging data. As may be understood from FIG. 3, a user interface (e.g., 300, 305) may direct a user to capture one or more images of a particular portion of their face in order to provide the system with the facial imaging data. This may include for example, a front view of the user's face (300), a side view 305 of the user's face, or any other view of combination of views of the user's face. In various aspects, the user interface includes one or more interactive elements for initiating the image capture.

Figure 4:
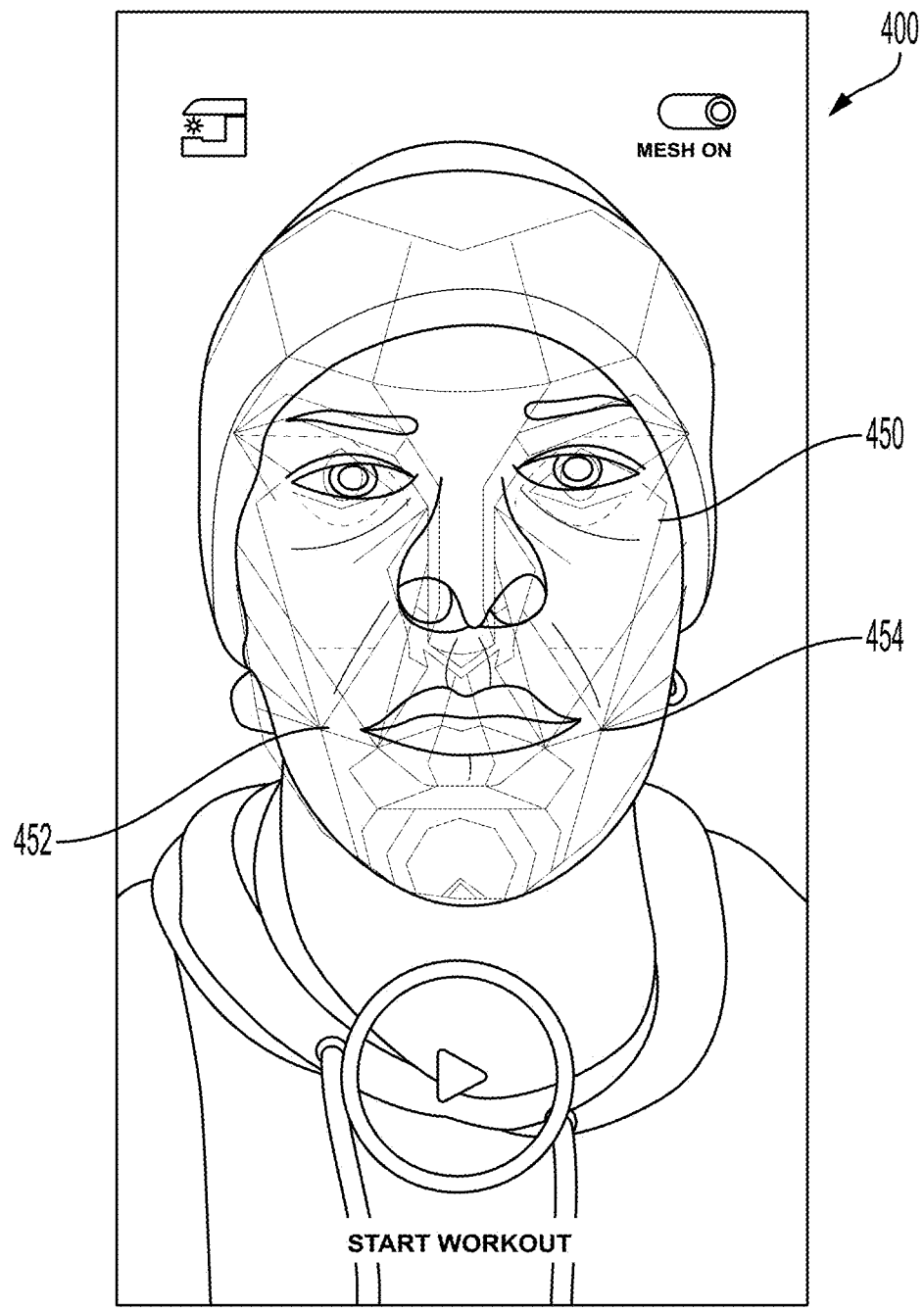
FIG. 4 depicts an example of a facial imaging data analysis interface in accordance with various aspects of the present disclosure.

At operation 204, the Facial Scanning and Analysis Module 200 analyzes facial imaging data. In various aspects, analyzing the facial imaging data includes identifying key points in the facial imaging data. In some aspects, each key point may correspond to a particular portion of a face. In particular aspects, each key point 452 may include a corresponding key point 454 on an opposing portion of the user' face. In particular aspects, a set of key points that define each feature of the user's face may form a mesh 450 defined by: (1) a perimeter of the user's face detected from the imaging data; and (2) made up of each identified feature as an intersection point defined by each identified key point. In some aspects, the system may generate a visual representation of the mesh 450 for display on the interface 400, as shown in FIG. 4.

In some aspects, when analyzing the facial imaging data, the system may determine a relative position of each key point with respect to one or more other key points in the facial image. For example, the system may determine a relative position of one or more adjacent key points to determine: (1) a distance between particular key points; (2) a relative location of particular key points with respect to the facial structure; (3) etc.

In some aspects, the system may utilize a machine-learning model such as a convolutional neural network for identifying key points of the user's face within the imaging data. Here, the convolutional neural network can be used to identify various key points that may be shown in the imaging data and make up distinct points on the user's face. For instance, the facial imaging data may include different portions of the face that the system can track the movement of, and relative position of in order to make determinations described herein with respect to facial defects and identify particular facial movements. For example, such objects may involve individuals portions of the face that are visible in the imaging data.

According to particular aspects, the machine-learning model used for processing the facial imaging data generates a feature representation (e.g., a feature vector) having components representing different points on the user's face that may be present in the imaging data. Each component may provide a prediction (e.g., a prediction value) as to whether each particular key point in a set of key points that define the user's face are present in the imaging data (e.g., image, video, etc.) and where. Therefore, the machine learning model may include an ensemble of classifiers in which each classifier is used in generating a prediction as to whether a particular key point is present in the imaging data and in what location.

In other aspects, the system may utilize any other suitable image processing technique to: (1) identify at least a portion of the individual's face in image content; and (2) identify one or more key points of the individual's face on the portion of their face visible in the image(s).

At operation 206, the Facial Scanning and Analysis Module 200 identifies facial defects based on the analysis. In some aspects, the system is configured to compare one or more facial key points to identify one or more facial defects. For example, the system may be configured to: (1) determine a facial orientation within the image (e.g., an angle at which the individual's head is positioned within the image); (2) identify a relative position of one or more coordinating key points (e.g., 452, 454), which may, for example, be on opposing sides of the individual's face, on the same side of the individual's face, etc.; and (3) determine whether the user's face has a defect based on the relative positioning. In some aspects, a facial defect may include, for example: (1) a facial asymmetry; (2) a facial muscle imbalance (i.e., one or more facial muscles having a large or smaller mass than expected or than a coordinating muscle on the user's face); (3) a facial injury (e.g., resulting from a stroke, surgical procedure, scarring, nerve damage, etc.); and/or (4) any other defect such as any facial issue that a user may desire to or be able to correct through a series of particular facial motions over time (e.g., facial exercises).

At operation 208, the Facial Scanning and Analysis Module 200 stores data related to the analysis, defects, and facial imaging data. In various aspects, the system may store the data in any suitable computer memory (e.g., such as locally on the user device 120), in the one or more data repositories 140, or in any suitable computer-readable medium within the system 100. In various aspects, the system 100 may store one or more facial images (i.e., 'before' images), data related to an extend of a particular identified defect (e.g., a percentage off of symmetry of a particular facial feature, a size difference between one or more facial features, etc.). In various aspects, storing the data related to the analysis, defects, and facial imaging data may enable the system to track a user's progress while taking part in a facial exercise/movement program (i.e., to monitor a change in a defect, progress toward a goal, etc.). The system may, for example, repeat the facial imaging data analysis process over time with newly acquired facial imaging data (e.g., newly captured images, video, etc. comprising at least a portion of the user's face) and compare the new data and/or analysis against prior data and/or analysis.

For illustrative purposes, the Facial Scanning and Analysis Module 200 described with reference to implementations described above with respect to one or more examples described herein. Other implementations, however, are possible. In some aspects, the steps in FIG. 2 may be implemented in program code that is executed by one or more computing devices such as the facial image processing and analysis computing system 100, the user device 120, or other system in FIG. 1. In some aspects, one or more operations shown in FIG. 2 may be omitted or performed in a different order. Similarly, additional operations not shown in FIG. 2 may be performed.

Facial Movement Tracking Module

Figure 5:
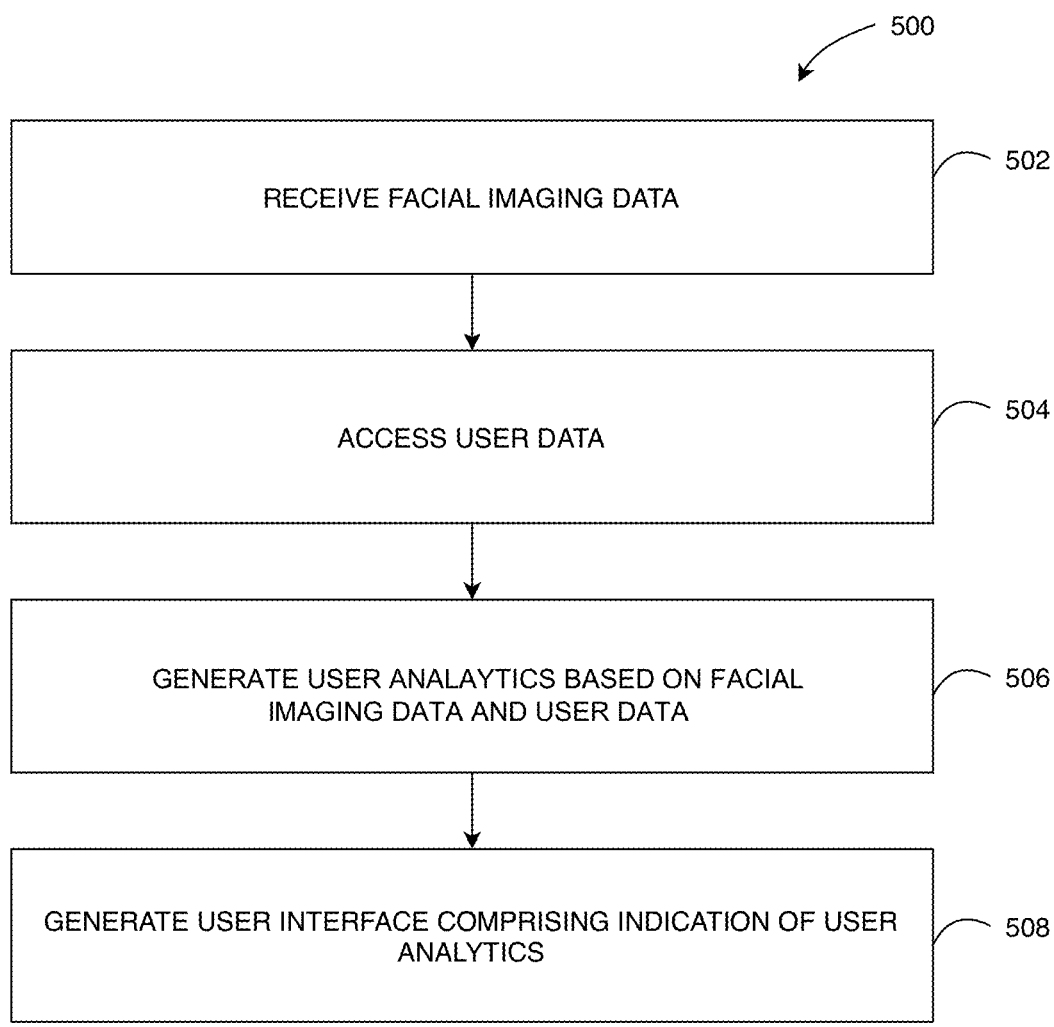
FIG. 5 depicts an example of a process for tracking facial movements of an individual in accordance with various aspects of the present disclosure.

Turning now to FIG. 5, additional details are provided regarding a Facial Movement Tracking Module 500. For instance, the flow diagram shown in FIG. 5 may correspond to operations executed by computing hardware found in facial image processing and analysis computing system 100 as it executes the Facial Movement Tracking Module 500.

At operation 502, the Facial Movement Tracking Module 500 receives facial imaging data. In various aspects, the Facial Scanning and Analysis Module 200 is configured to receive the facial imaging data in any suitable manner, such as via the software application 122 executing on a user device 120 (e.g., via a network 150). For example, the Facial Movement Tracking Module 500 may receive the facial imaging data from an imaging device on the user device 120 (e.g., a smartphone's built-in camera). In particular aspects, the facial imaging data includes a series of facial images (e.g., still and/or video images) taken of at least a portion of the user's face, head, neck, etc. while the user is performing a facial movement.

At operation 504, the Facial Movement Tracking Module 500 accesses and/or receives user data. In various aspects, the Facial Movement Tracking Module 500 may receive and/or access user data provided by the user. In other aspects, the Facial Movement Tracking Module 500 may interface with one or more third party computing systems 170 to access the user data. In still other embodiments, the Facial Movement Tracking Module 500 may receive user data from one or more wearable devices worn by the user. In some aspects, the user data may include, for example: (1) heart rate; (2) height; (3) gender; (4) weight; (5) diet; (6) food intake data (e.g., what the user has eaten); (7) body mass index (BMI); (8) fitness goal data; (9) facial defect data; (10) injury history data; (11) facial scan data (e.g., facial analysis and imaging data determined with respect to the Facial Scanning and Analysis Module 200 discussed above); and/or (12) any other suitable data related to the user that the system 100 may use, for example, in determining and/or generating more accurate user analytics discussed herein. For example, as will be understood by one skilled in the art, the system may 100 generate more accurate calorie burn data for a particular set of movements when taking into account certain data that is specific to the user (e.g., height, weight, gender, age, BMI, heart rate, VO2 Max, etc.).

In some aspects, the system 100 may receive the user data by accessing user health readings form a particular wearable device (e.g., heart rate via a heart monitor or smart watch or other wearable. In some aspects, the system may access one or more third party computing systems 170 (e.g., via a suitable application programming interface) to retrieve particular user data. For example, the system may access data collected a nutrition tracking application to identify particular food consumed by the user, food intake timing, etc.

At operation 506, the Facial Movement Tracking Module 500 generates user analytics based on facial imaging data and the user data. The analytics may include, for example: (1) a number of repetitions completed of a particular movement; (2) a form of the particular movement; (3) a number of units of energy (e.g., calories) burned by the user while performing the identified movements; (4) a hold time of each movement (e.g., a length of time at which each repetition was held such as for a biting down, squeezing, flexing, etc. motion); (5) a length of time recorded for the set of facial movements; (6) a time between each repetition; and/or (7) any other suitable analytics related to the identification and tracking of one or more user movements (i.e., facial movements) contained in the facial imaging data.

In various aspects, the system 100 may process the facial imaging data and the user data movement using a rules-based model, a machine-learning model, or both to generate an estimate of a number of repetitions completed by the user during a time over which the facial imaging data was captured. For example, the rules-based model, machine learning model, or combination of both may be configured to generate a prediction as to a likelihood of an occurrence of any particular movement including a desired facial movement, in addition to a number of each movement that occurred.

For example, according to particular aspects, the system may use a rules-based model to determine the number of repetitions. The rules-based model may comprise a set of rules that defines a particular identified motion as an individual repetition. For example, the set of rules may define one or more rules for assigning repetition values for a particular motion in response to identifying at least a particular portion of the motion has been completed. Accordingly, the system may maintain the set of rules in some type of data storage, from which the system can access the set of rules for determining the number of repetitions.

According to other aspects, system may utilize a machine learning model in making the determination. Here, the machine learning model may be trained using historical data on identified facial movements to determine: (1) a type of movement identified; (2) a number of repetitions of that movement performed; (3) etc. In various aspects, the training data may be derived from a plurality of users for whom facial movement data has been analyzed. Accordingly, the machine learning model may be configured using a variety of different types of supervised or unsupervised trained models such as, for example, support vector machine, naive Bayes, decision tree, neural network, and/or the like.

In particular embodiments, the system may implement one or more neural networks to perform any of the big data processing techniques described herein. A neural network, according to various embodiments, comprises: (1) a plurality of nodes that mimic the operation of the human brain; (2) a training mechanism that analyzes supplied information, and (3) a facial movement determination engine for determining a type and quantity of particular performed movement. In various embodiments, each of the nodes comprises one or more weighted input connections, at least one transfer function that combines the inputs, and an output connection. In particular embodiments, the neural network is a variational AE neural network, a denoising AE neural network, or any other suitable neural network.

In various embodiments, the machine learning model and/or neural network may utilize one or more of: (1) user age; (2) user gender; (3) user fitness level; (4) user diet data; (5) identified exercise device (e.g., jaw exercise device) utilized during the facial movements; (6) the presence of one or more facial defects of the user; (7) face shape; (8) face size; (9) size of one or more individual facial features; and/or (10) any other suitable factors. In some aspects, the system may use these factors as inputs related to determining facial movement repetitions and other user analytics (e.g., calorie burn, form, etc.). In particular aspects, the training data may enable the neural network and/or other machine learning model to apply identified relationships between the identified movements (e.g., and number thereof) and user data (e.g., age, gender, weight, face shape, etc.) to provide more accurate, user-specific analytics related to the identified facial movements (e.g., calories burned, number of repetitions, etc.). As discussed herein, the number of muscles within the face make it technically challenging to identify particular movements from imaging data (e.g., when compare to straightforward, linear movements such as bicep curls or other larger muscle movements). The subtleties of facial movements may, for example, make it technically difficult to distinguish between different types of facial movements (e.g., chomping versus biting versus clenching, etc.). This can be especially true, for example, when a user is utilizing a jaw exercise device which may at least partially obscure the facial muscles while recording a particular exercise or set of exercises (e.g., while capturing facial imaging data for processing by the system).

Figure 6:
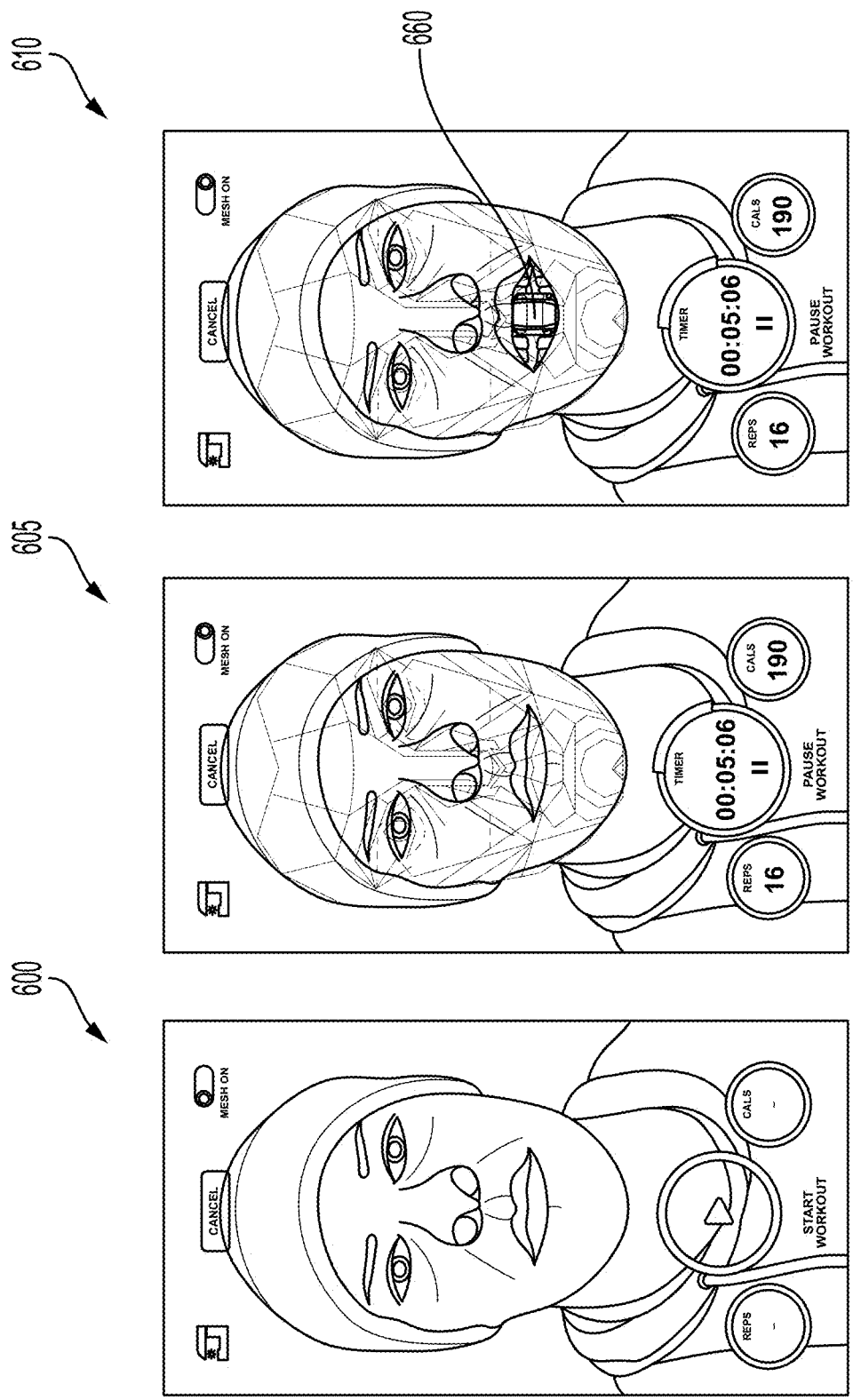
FIG. 6 depicts an example of facial imaging data capture interfaces according to yet another aspect of the present disclosure.

At operation 508, the Facial Movement Tracking Module 500 generates a user interface comprising an indication of the user analytics and provides the interface for display on a computing device (e.g., user device 120). In some aspects, the system 100 may incorporate the analytics into the facial imaging data. For example, FIG. 6 depicts exemplary user interfaces 600, 605, 610 depicting generated analytics (e.g., in addition to facial imaging data). In various aspects, as shown in FIG. 6, a user interface 600 may include one or more indicia for initiating the analytic generation described herein. Selection, by a user, of a "start workout" button on an interface 600 may initiate generation of any analytic described herein based on the imaging data and user data discussed above. In response to selection of the "start workout" button, the system 100 may, as may be understood from the interface 605 in FIG. 6, begin generating analytics and displaying an indication of the generated analytics on the user interface 605. The system 100 may, for example, generate and display a user interface 605 that includes the indication of a number of repetitions captured (e.g., 16) and a number of calories burned 190) during a particular workout. As may be understood in light of this disclosure, the repetitions determined may be user specific (i.e., as determined by the machine learning model, neural network, etc. in light of the image processing and user data) as well as workout specific (i.e., the number of repetitions may be determined based on a particular desired repetition type for tracking purposes, such as chomping, biting down, biting and holding, tensing particular muscles in the face, etc.). The calories burned (190) displayed on the user interface 605 may also be user-specific as determined through processing by the machine learning model, neural network, etc. in light of the image processing and user data. Different individuals may, for example, burn different numbers of calories from performing the same movements. The system 100, through operation of the machine learning model, neural network, rules based model, or combination thereof, may derive a calorie burn number that is specific to the user in light of particular data fed to the machine learning model, neural network, rules based model, or combination thereof (e.g., age, physical condition, injury history, weight, diet, etc.).

In a particular example, the act of chomping may cause an individual to salivate, which can affect the user's metabolic rate. Metabolic rate can, in turn, affect a number of calories burned by the individual. By factoring in whether the user has recently eaten, the system 100 may, for example, determine that initiating a chomping exercise might cause a spike in metabolic rate when the user has not recently eaten (as determined by user data accessed regarding the user's diet, meal timing, recently entered meals in a meal tracking application or system, etc.). The determination of a metabolic rate spike may affect the determination of the number of calories burned during a particular sequence of movements.

The interface 610 shown in FIG. 6 includes a visible jaw exercise device 660 in the mouth of the user. The system may, for example, analyze the facial imaging fata to identify a particular jaw exercise device in the mouth of the user. The system may then determine, based on the analysis, a type of the jaw exercise device. When generating the user analytics, the system may then use the presence of the jaw exercise device (e.g., by using the type of device as input in the machine learning model, neural network, rules-based model, etc.; by modifying a determined analytic based on the identified device; etc.). The system may, for example, identify the device in any suitable manner such as through a color of the device, user input, a size/shape of the device, a unique indicia on the device such as a machine-readable indicia, etc.

Figure 7:
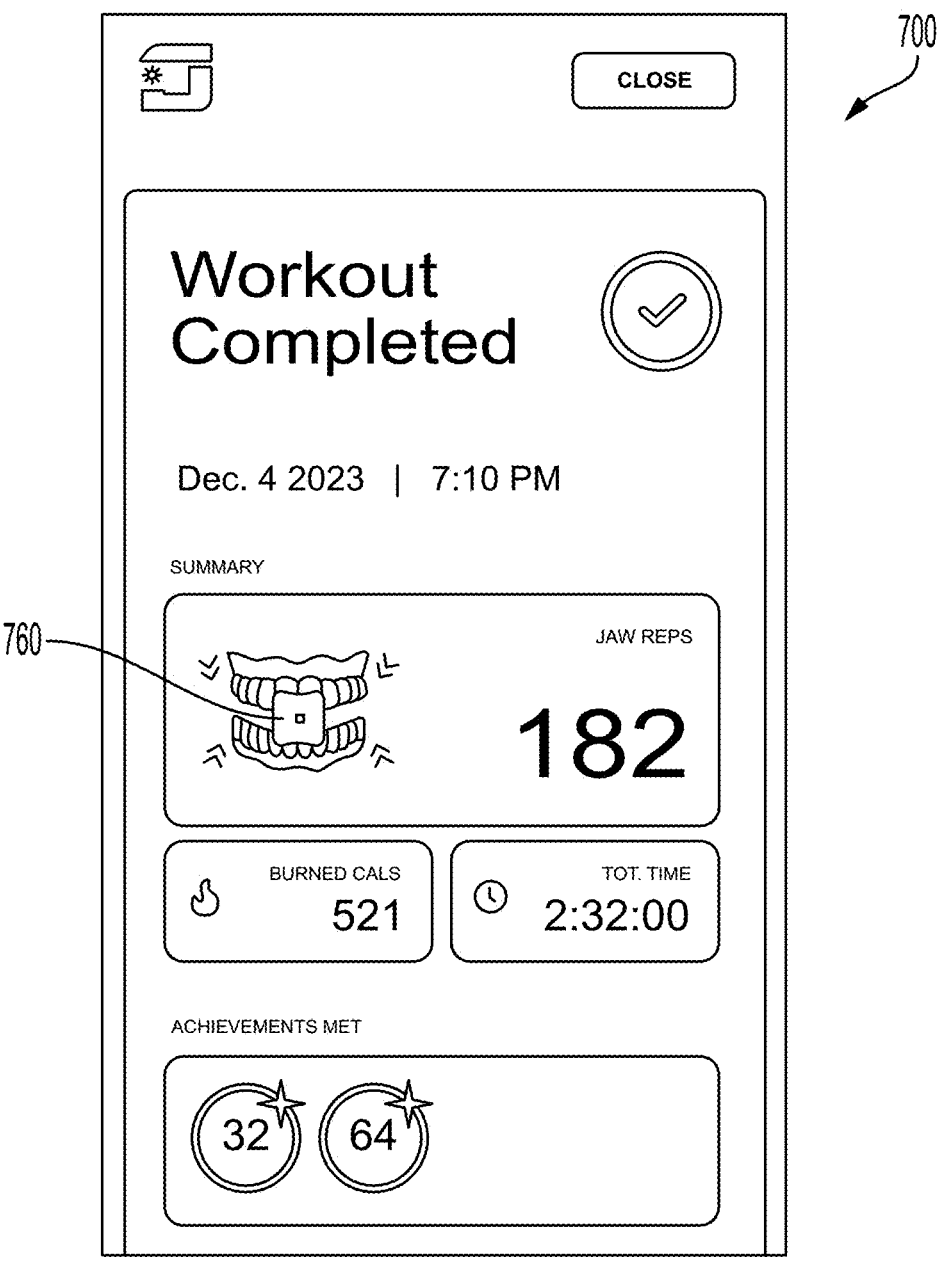
FIG. 7 depicts an example of customized motion summary interface according to yet another aspect of the present disclosure.

FIG. 7 depicts an exemplary summary interface 700 including a workout summary for a particular date. As may be understood form this figure, the interface 700 includes an indication of a number of repetitions performed, calories burned, time performing the exercises, as well as progress towards one or more goals in the form of achievements. The interface 700 also includes a visual indication of the jaw exercise device 160 utilized in the exercise.

For illustrative purposes, the Facial Movement Tracking Module 500 described with reference to implementations described above with respect to one or more examples described herein. Other implementations, however, are possible. In some aspects, the steps in FIG. 5 may be implemented in program code that is executed by one or more computing devices such as the facial image processing and analysis computing system 100, the user device 120, or other system in FIG. 1. In some aspects, one or more operations shown in FIG. 5 may be omitted or performed in a different order. Similarly, additional operations not shown in FIG. 5 may be performed.

Facial Modification Progress Tracking Module

Figure 8:
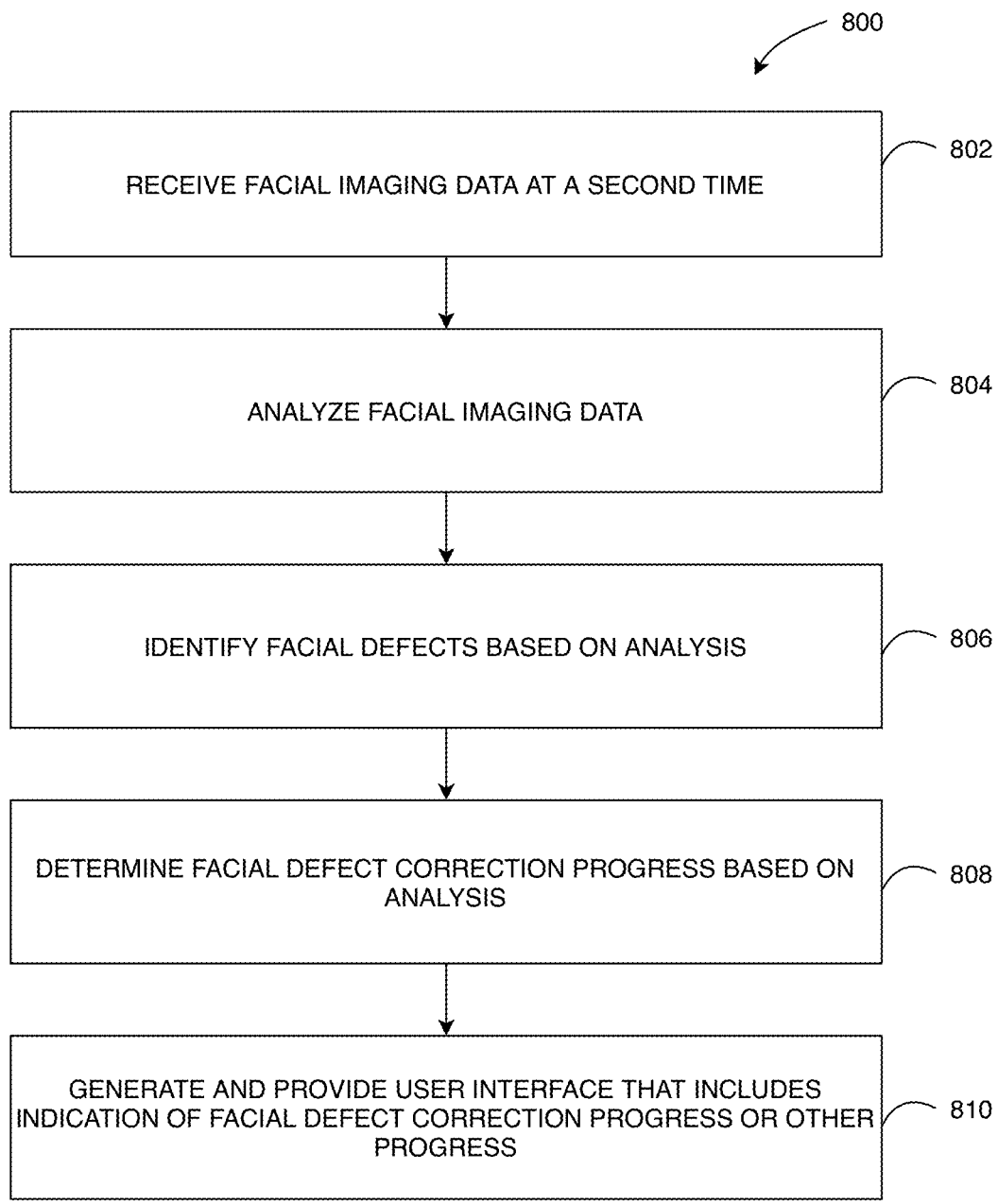
FIG. 8 depicts an example of a process for tracking facial modification progress in accordance with various aspects of the present disclosure.

Turning now to FIG. 8, additional details are provided regarding a Facial Modification Progress Tracking Module 800. For instance, the flow diagram shown in FIG. 8 may correspond to operations executed by computing hardware found in facial image processing and analysis computing system 100 as it executes the Facial Modification Progress Tracking Module 800.

At operation 802, the Facial Modification Progress Tracking Module 800 receives facial imaging data at a second time. In various aspects, the second time may be any time after the first time referred to with respect to the Facial Scanning and Analysis Module 200. By receiving additional facial imaging data at a later time, the Facial Modification Progress Tracking Module 800 may enable the system to track a user's progress toward one or more metrics. For example, the one or more metrics may include improvement towards a goal, progress along a particular planned set of facial movements, progress toward remedying or improving a particular facial defect, etc. In various aspects, the Facial Modification Progress Tracking Module 800 is configured to receive the facial imaging data in any suitable manner, such as via the software application 122 executing on a user device 120 (e.g., via a network 150). In particular aspects, the facial imaging data includes progress facial imaging data for a user in the process of performing various facial movements, a user that has completed a movement program (e.g., exercise program), a user that is in the process of completing a movement program, etc.

At operation 804, the Facial Modification Progress Tracking Module 800 analyzes the facial imaging data. In various aspects, analyzing the facial imaging data includes identifying key points in the facial imaging data. In some aspects, each key point may correspond to a particular portion of a face. In particular aspects, each key point 452 may include a corresponding key point 454 on an opposing portion of the user' face. In particular aspects, a set of key points that define each feature of the user's face may form a mesh 450 defined by: (1) a perimeter of the user's face detected from the imaging data; and (2) made up of each identified feature as an intersection point defined by each identified key point. In some aspects, the system may generate a visual representation of the mesh 450 for display on the interface 400, as shown in FIG. 4.

In some aspects, when analyzing the facial imaging data, the system may determine a relative position of each key point with respect to one or more other key points in the facial image. For example, the system may determine a relative position of one or more adjacent key points to determine: (1) a distance between particular key points; (2) a relative location of particular key points with respect to the facial structure; (3) etc.

In some aspects, the system may utilize a machine-learning model such as a convolutional neural network for identifying key points of the user's face within the imaging data. Here, the convolutional neural network can be used to identify various key points that may be shown in the imaging data and make up distinct points on the user's face. For instance, the facial imaging data may include different portions of the face that the system can track the movement of, and relative position of in order to make determinations described herein with respect to facial defects and identify particular facial movements. For example, such objects may involve individuals portions of the face that are visible in the imaging data.

According to particular aspects, the machine-learning model used for processing the facial imaging data generates a feature representation (e.g., a feature vector) having components representing different points on the user's face that may be present in the imaging data. Each component may provide a prediction (e.g., a prediction value) as to whether each particular key point in a set of key points that define the user's face are present in the imaging data (e.g., image, video, etc.) and where. Therefore, the machine learning model may include an ensemble of classifiers in which each classifier is used in generating a prediction as to whether a particular key point is present in the imaging data and in what location.

In other aspects, the system may utilize any other suitable image processing technique to: (1) identify at least a portion of the individual's face in image content; and (2) identify one or more key points of the individual's face on the portion of their face visible in the image(s).

At operation 806, the Facial Modification Progress Tracking Module 800 identifies facial defects based on the analysis 804. In some aspects, the system is configured to compare one or more facial key points to identify one or more facial defects. For example, the system may be configured to: (1) determine a facial orientation within the image (e.g., an angle at which the individual's head is positioned within the image); (2) identify a relative position of one or more coordinating key points (e.g., 452, 454), which may, for example, be on opposing sides of the individual's face, on the same side of the individual's face, etc.; and (3) determine whether the user's face has a defect based on the relative positioning. In some aspects, a facial defect may include, for example: (1) a facial asymmetry; (2) a facial muscle imbalance (i.e., one or more facial muscles having a large or smaller mass than expected or than a coordinating muscle on the user's face); (3) a facial injury (e.g., resulting from a stroke, surgical procedure, scarring, nerve damage, etc.); and/or (4) any other defect such as any facial issue that a user may desire to or be able to correct through a series of particular facial motions over time (e.g., facial exercises).

At operation 808, the Facial Modification Progress Tracking Module 800 determines facial defect correction progress based on the analysis. In some aspects, they system is configured to track facial defect correction over time by comparing a condition of one or more defects identified at the second time, to a condition of the defects at the first time. For instance, the system may identify a 1.5 cm facial asymmetry at a first time, and (after a course of corrective exercise) identify that the facial asymmetry is down to 0.9 cm.

Figure 9:
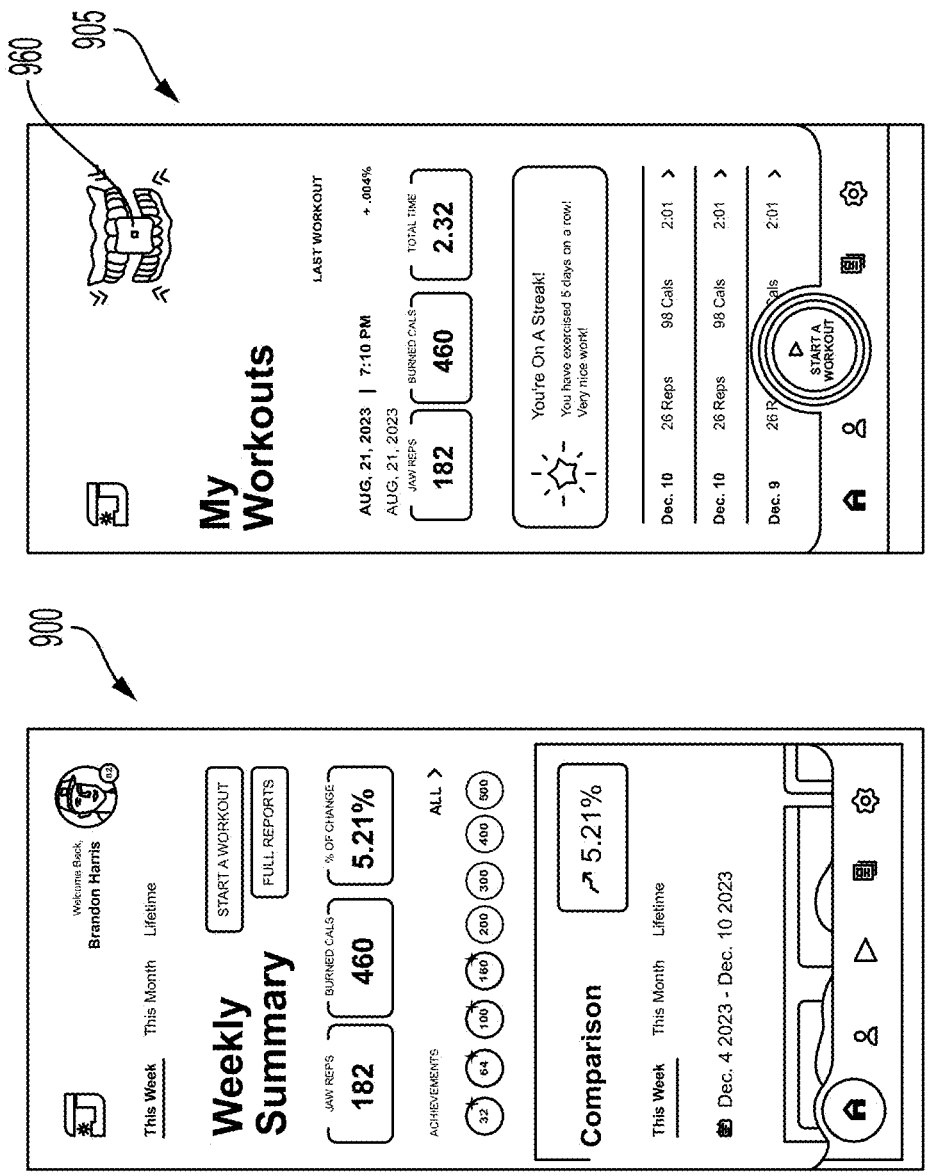
FIG. 9 depicts an example of a customized motion summary and progress interface according to yet another aspect of the present disclosure.

At operation 810, the Facial Modification Progress Tracking Module 800 generates and provides a user interface that includes an indication of the facial defect correction progress or other progress. FIG. 9 depicts an exemplary interface 900 showing progress over time for a user's facial exercises. This includes total repetitions and calories across all recorded exercises or for a particular time period. Interface 905 depicts individual workout details from different days. By providing such interfaces, the system may enable a user to view workout history, and workout details that the system has recorded at different time periods. Such interface may, for example, reducing cumbersome or time-consuming processes for accessing such system generated data generated from different sources and at different times.

Figure 10:
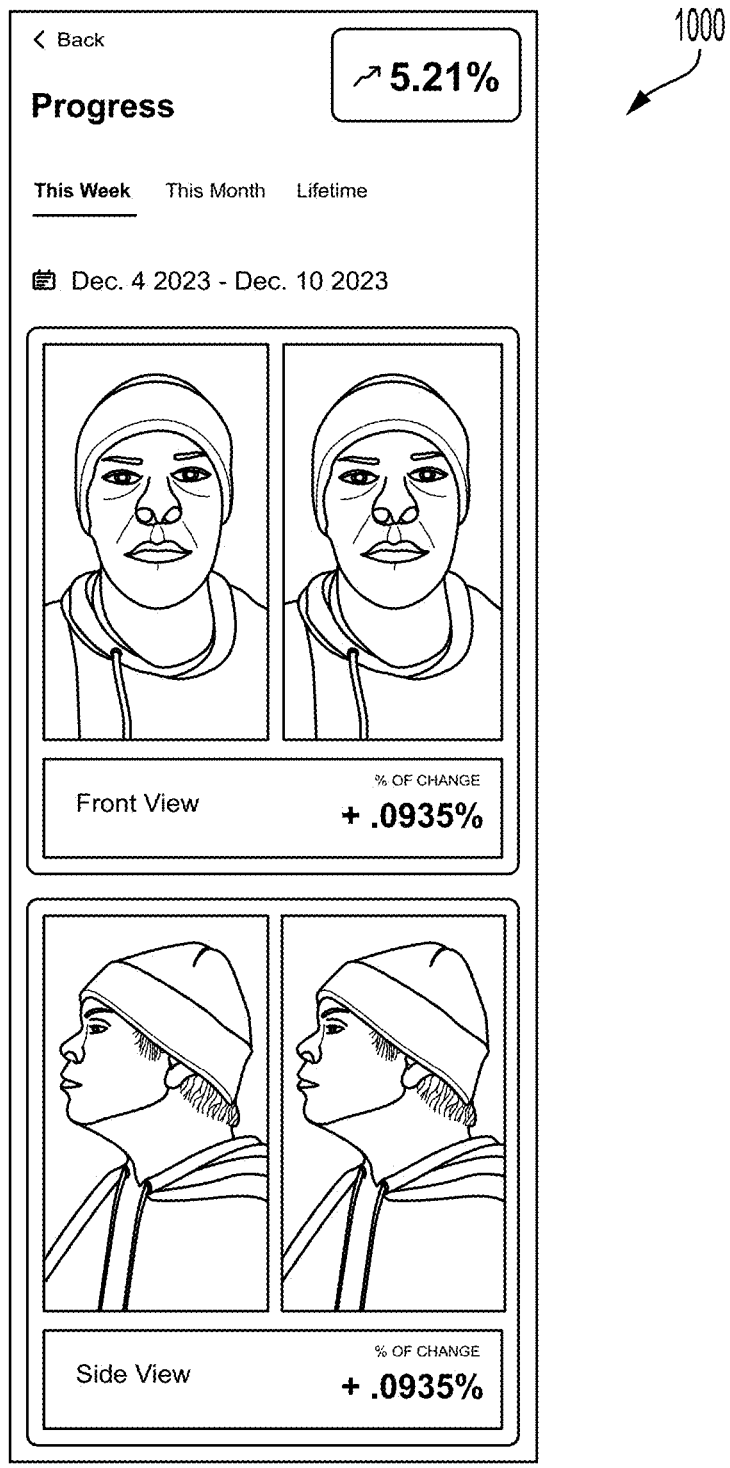
FIG. 10 depicts an example of a progress interface according to yet another aspect of the present disclosure.

FIG. 10 depicts defect progress interface 1000 which includes before and after imaging as well as a percentage change (e.g., improvement) toward a particular defect correction or goal.

For illustrative purposes, the Facial Modification Progress Tracking Module 800 described with reference to implementations described above with respect to one or more examples described herein. Other implementations, however, are possible. In some aspects, the steps in FIG. 8 may be implemented in program code that is executed by one or more computing devices such as the facial image processing and analysis computing system 100, the user device 120, or other system in FIG. 1. In some aspects, one or more operations shown in FIG. 8 may be omitted or performed in a different order. Similarly, additional operations not shown in FIG. 8 may be performed.

Facial Exercise Customization Module

Figure 11:
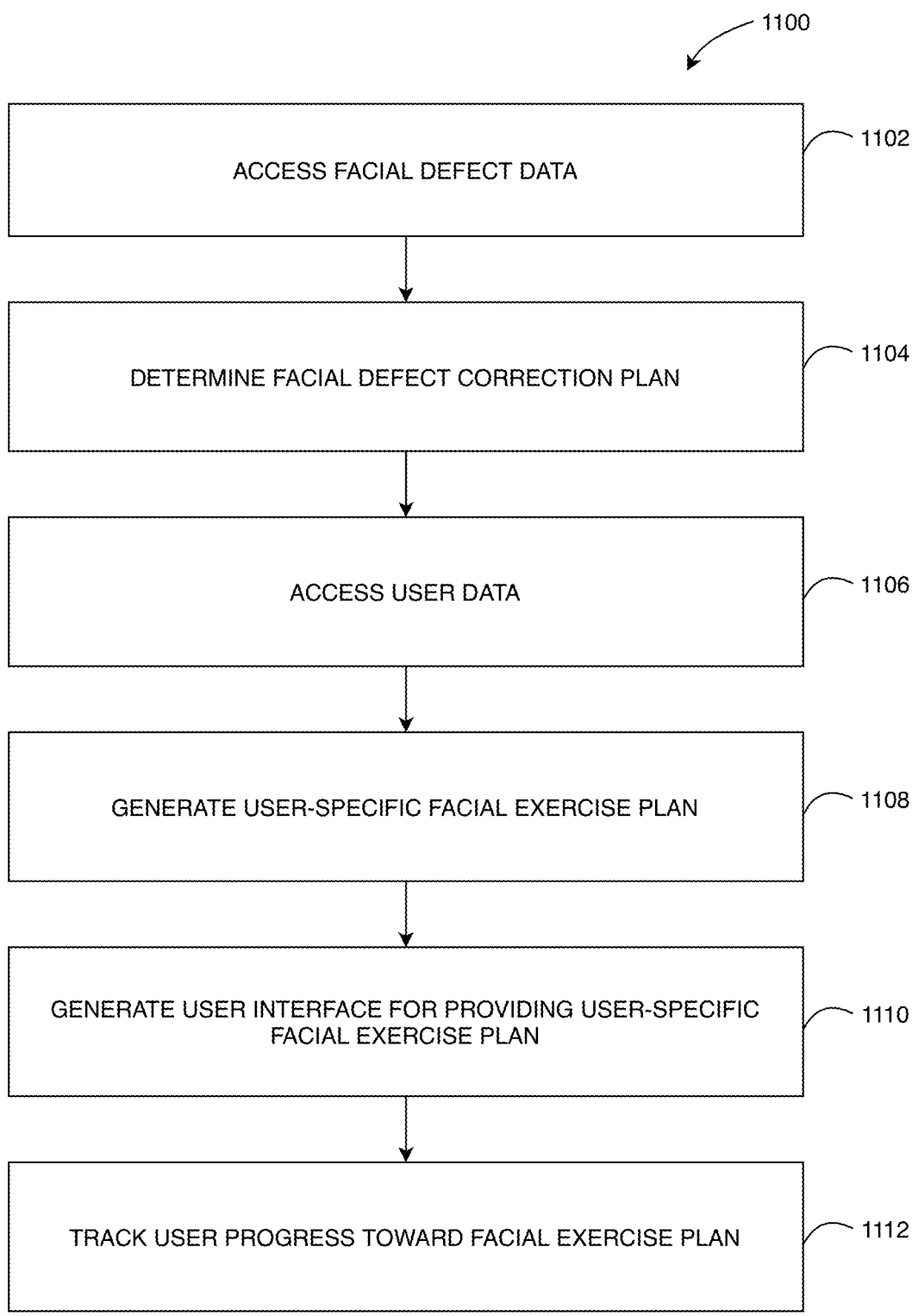
FIG. 11 depicts an example of a process for generating a user-specific customized facial exercise plan in accordance with various aspects of the present disclosure.

Turning now to FIG. 11, additional details are provided regarding a Facial Exercise Customization Module 1100. For instance, the flow diagram shown in FIG. 11 may correspond to operations executed by computing hardware found in facial image processing and analysis computing system 100 as it executes the Facial Exercise Customization Module 1100.

At operation 1102, the Facial Exercise Customization Module 1100 accesses facial defect data. The facial defect data may, for example, include any facial defect data identified with respect to the other modules described herein. In some aspects, a facial defect may include, for example: (1) a facial asymmetry; (2) a facial muscle imbalance (i.e., one or more facial muscles having a large or smaller mass than expected or than a coordinating muscle on the user's face); (3) a facial injury (e.g., resulting from a stroke, surgical procedure, scarring, nerve damage, etc.); and/or (4) any other defect such as any facial issue that a user may desire to or be able to correct through a series of particular facial motions over time (e.g., facial exercises).

At operation 1104, the Facial Exercise Customization Module 1100 determines a facial defect correction plan. In some aspects, the facial defect correction plan may include any plan designed to address the particular defect to be addressed. For example, a facial asymmetry correction plan may be designed to increase a size of muscles on one portion of a user's face in order to make that portion of the user's face more even with an opposing portion of the face. A plan to correct a defect involving an undesirable jawline may involve strengthening one or more muscles along the jawline of the user. In some aspects, the plan may identify a particular set of muscles that are sought to be modified through a customized set of exercises in order to address the facial defect. In various aspects, in response to identifying a particular defect involving a particular portion of a user's face, a particular muscle or set of muscles in the user's face, etc., the system may determine a plan that involves modification (i.e., strengthening, bulking, leaning out, etc.) of those identified muscle(s)/facial portions.

At operation 1106, the Facial Exercise Customization Module 1100 access user data. In some aspects, the user data may include, for example: (1) heart rate; (2) height; (3) gender; (4) weight; (5) diet; (6) food intake data (e.g., what the user has eaten); (7) body mass index (BMI); (8) fitness goal data; (9) facial defect data; (10) injury history data; (11) facial scan data (e.g., facial analysis and imaging data determined with respect to the Facial Scanning and Analysis Module 200 discussed above); and/or (12) any other suitable data related to the user that the system 100 may use, for example, in providing a more effective set of exercises for addressing an identified defect.

At operation 1108, the Facial Exercise Customization Module 1100 generates a user-specific facial exercise plan. In some aspects, the user-specific facial exercise plan includes a set of facial movements (including a number, duration, whether to include one or more jaw exercise devices or other accessories, etc.) and a schedule for performing them. When generating the user-specific plan, the system may process the facial defect correction plan, the user data, and historical user facial movement data using a rules-based model, a machine-learning model, or both to generate the plan. For example, the rules-based model, machine learning model, or combination of both may be configured to process the facial defect correction plan, the user data, and historical user facial movement data, and/or the like in generating a plan designed to correct the identified defect in the user's facial structure (e.g., by determining which particular facial movements in what quantity according to what schedule could be used to address the user's identified facial defect). For example, the rules-based model, machine learning model, or combination of both may be configured to generate the plan based on the identified defect that satisfies the set of rules indicating the user's availability to perform facial movements, ability to perform facial movements, etc. For example, the system may generate a plan based on a sets of movements performed by other users for the same or similar facial defects that have resulted in improvement or correction of the identified defect. In doing so, the system may generate the plan by utilizing a limited set of past user data by identifying users that are similarly situated to the reference individual (i.e., the individual for whom the plan is being generated). In this way, the system may be configured to generate an improvement plan that may increase the likelihood of success of improving and/or addressing the identified defect for the specific user. In some aspects, the set of rules may include particular movements to preclude (e.g., because of user injury the precludes such movements), timing restrictions, and the like. In particular aspects, the set of rules may define a time limit for each set of determined facial movements in the plan (e.g., by generating a plan that includes progressive sets of facial movements none of which are longer than a particular amount of time, such as five minutes per day).

According to other aspects, the system 100 may utilize a machine learning model in generating an improvement/exercise plan. Here, the machine learning model may be trained using historical user data including improvement progress for other users with identified facial defects (i.e., similar defects such as similar imbalance, asymmetry, etc.). Accordingly, the machine learning model may be configured using a variety of different types of supervised or unsupervised trained models such as, for example, support vector machine, naive Bayes, decision tree, regression, neural network, and/or the like.

According to still other aspects, the system may use a combination of the rules-based model and the machine learning model in generating a recommendation. In some aspects, the generated plan may provide a set of exercises and a schedule for performing them.

At operation 1110, the Facial Exercise Customization Module 1100 generates a user interface for providing the user-specific facial exercise plan. The interface may provide an indication of particular exercises to be performed, as well as a manner for inputting the user's progress or otherwise providing an indication that the user is performing at least a particular portion of the plan.

At operation 1112, the Facial Exercise Customization Module 1100 tracks user progress toward the facial exercise plan. The system may, for example, utilize the Facial Movement Tracking Module 500, the Facial Modification Progress Tracking Module 800, or the like to track the user's facial movements during each prescribed set of facial exercises as the user progresses through the customized plan. In this way, the system may track the user's completion of each specific movement at the required (i.e., desired) number of repetitions and techniques. The Facial Exercise Customization Module 1100 may then generate alerts in response to determining that the user has fallen behind or is missing particular movements, prompt the user to take progress pictures (e.g., updated facial images) for progress comparison, etc.

For illustrative purposes, the Facial Exercise Customization Module 1100 described with reference to implementations described above with respect to one or more examples described herein. Other implementations, however, are possible. In some aspects, the steps in FIG. 11 may be implemented in program code that is executed by one or more computing devices such as the facial image processing and analysis computing system 100, the user device 120, or other system in FIG. 1. In some aspects, one or more operations shown in FIG. 11 may be omitted or performed in a different order. Similarly, additional operations not shown in FIG. 11 may be performed.

Facial Exercise Model Training Module

Figure 12:
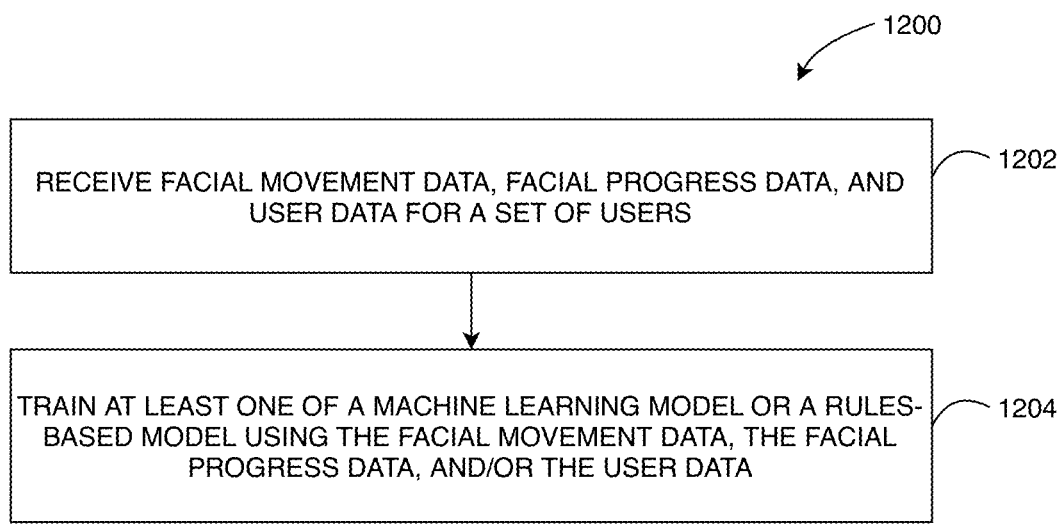
FIG. 12 depicts an example of a process for providing training data to train a machine learning model for generating customized facial exercise/movement plans in accordance with various aspects of the present disclosure.

Turning now to FIG. 12, additional details are provided regarding a Facial Exercise Model Training Module 1200. For instance, the flow diagram shown in FIG. 12 may correspond to operations executed by computing hardware found in facial image processing and analysis computing system 100 as it executes the Facial Exercise Model Training Module 1200.

At operation 1202, the Facial Exercise Model Training Module 1200 receives facial movement data, facial progress data, and user data for a set of users (i.e., one or more users). The system may receive and/or access such data in response to one or more system users: (1) taking progress images; (2) recording image data of a particular facial movement session; (3) requesting customized facial movement plans; (4) etc. In some aspects, the system may receive any suitable movement data, progress data and user data described herein. In some aspects, the system may capture this data through execution of other system modules. In this way, the facial image processing and analysis computing system 100 may capture progress, movement, and user data from a plurality of different sources for a plurality of users, which may, for example, increase an accuracy of a model used to identify facial movements, generate customized movement plans, etc. In some aspects, identifying a suitable training program for any individual can be technically challenging, as each individual user is unique, has a unique set of requirements, and may respond differently to difference exercise routines. As such, by increasing the effectiveness of machine learning models, rules-based models, and the like, the system described herein can provide technical improvements to systems dedicated to generating such user-specific plans.

The Facial Exercise Model Training Module 1200 may then, at operation 1204, train at least one of a machine learning model or a rules-based model using the facial movement data, the facial progress data and/or the user data. In this way, the module may be trained to identify which particular set of facial movements result in better facial progress (e.g., toward correcting particular defects) for similar users. In this way, the module may determine particular movements that are less effective at addressing certain defects for certain types of individuals (e.g., such that those movements may be omitted from a training plan for such a user to address a certain defect) and which are more effective.

For illustrative purposes, the Facial Exercise Model Training Module 1200 described with reference to implementations described above with respect to one or more examples described herein. Other implementations, however, are possible. In some aspects, the steps in FIG. 12 may be implemented in program code that is executed by one or more computing devices such as the facial image processing and analysis computing system 100, the user device 120, or other system in FIG. 1. In some aspects, one or more operations shown in FIG. 12 may be omitted or performed in a different order. Similarly, additional operations not shown in FIG. 12 may be performed.

Facial Movement Tracking Model Training Module

Figure 13:
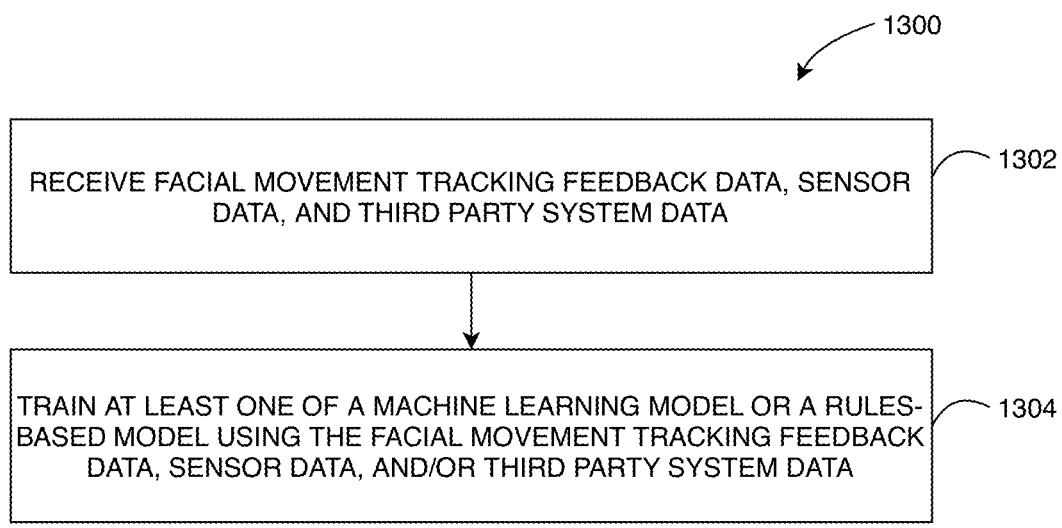
FIG. 13 depicts an example of a process for providing training data to train a machine learning model for tracking facial movement in accordance with various aspects of the present disclosure.

Turning now to FIG. 13, additional details are provided regarding a Facial Movement Tracking Model Training Module 1300. For instance, the flow diagram shown in FIG. 13 may correspond to operations executed by computing hardware found in facial image processing and analysis computing system 100 as it executes the Facial Movement Tracking Model Training Module 1300. In some aspects, the Facial Movement Tracking Model Training Module 1300 may train a model for identifying particular facial movements from facial imaging data.

At operation 1302, the Facial Movement Tracking Model Training Module 1300 receives facial movement tracking feedback data, sensor data, and/or third-party system data. In some aspects, the system may receive feedback from users regarding an accuracy of an identified number of repetitions. The system may further receive calorie burn and other data from one or more wearable devices or a third party system tracking calorie burn on behalf of a user (e.g., to compare to the determined number of calories burned through use of the machine learning models, neural networks, etc. described herein). In this way, the system may train a model to improve the accuracy of a model used to determine what movements (and in what quantities) were performed within facial imaging data.

The Facial Movement Tracking Model Training Module 1300 may then, at operation 1304, train at least one of a machine learning model or a rules-based model using the facial movement tracking feedback data, sensor data, and/or third party system data.

For illustrative purposes, the Facial Movement Tracking Model Training Module 1300 described with reference to implementations described above with respect to one or more examples described herein. Other implementations, however, are possible. In some aspects, the steps in FIG. 13 may be implemented in program code that is executed by one or more computing devices such as the facial image processing and analysis computing system 100, the user device 120, or other system in FIG. 1. In some aspects, one or more operations shown in FIG. 13 may be omitted or performed in a different order. Similarly, additional operations not shown in FIG. 13 may be performed.

Facial Movement Interface Interaction Module

Figure 14:
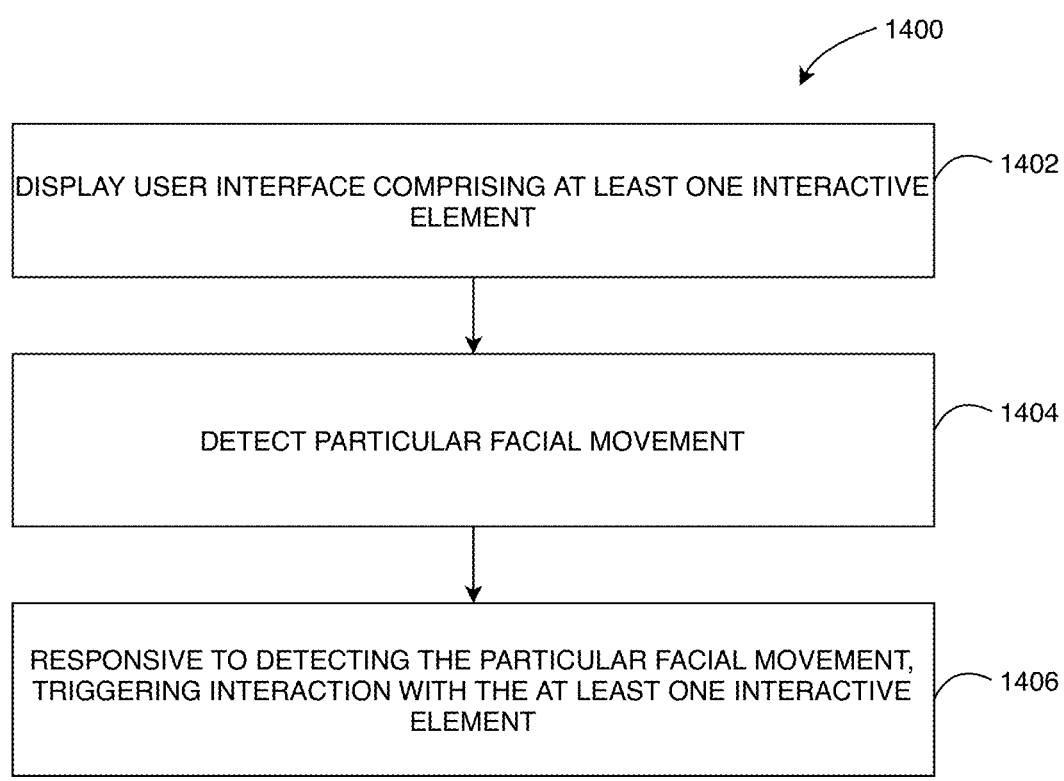
FIG. 14 depicts an example of a process for modifying a user interface based on identified facial movements in accordance with various aspects of the present disclosure.

Turning now to FIG. 14, additional details are provided regarding a Facial Interface Interaction Module 1400. For instance, the flow diagram shown in FIG. 14 may correspond to operations executed by computing hardware found in facial image processing and analysis computing system 100 as it executes the Facial Interface Interaction Module 1400.

At operation 1402, the Facial Interface Interaction Module 1400 displays a user interface comprising at least one interactive element. In any aspect described herein, the interactive element may include any element via which the user can provide input to the system (e.g., a button, selectable object, etc.)

Next, at operation 1404, the Facial Interface Interaction Module 1400 detects a particular facial movement. The system may for example detect the movement using any suitable technique described herein.

Response to detecting the particular facial movement, at operation 1406, the Facial Interface Interaction Module 1400 triggers an interaction with the at least one interactive element. In other aspects, the particular movement may have a correlated input for the user device 120. The system may, in such embodiments, provide the correlated input to the user device 120 in response to identifying the particular movement form the imaging data.

Figure 15:
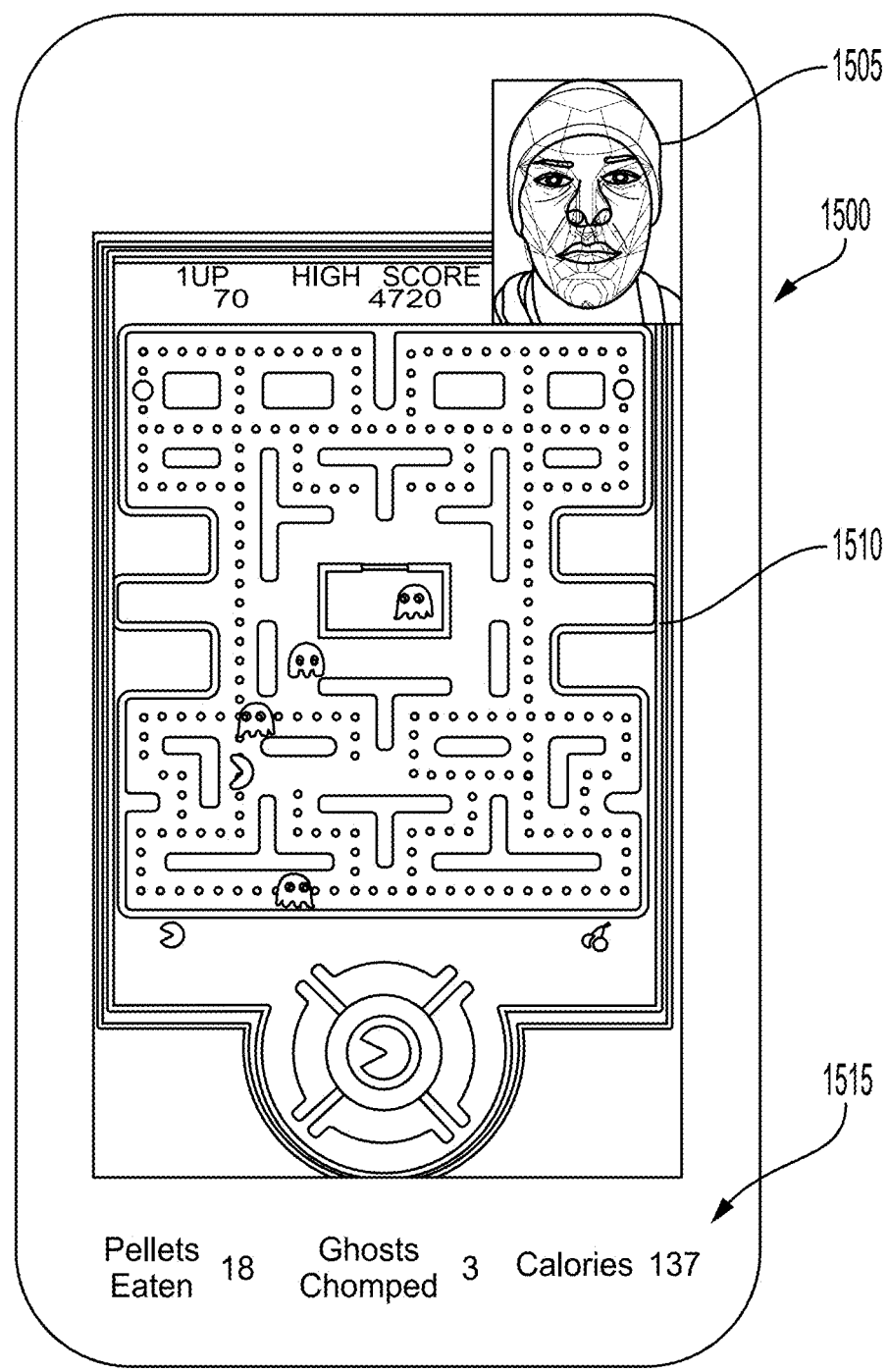
FIG. 15 depicts an example of an interactive interface according to various aspects of the present disclosure.

For example, FIG. 15 depicts an exemplary user interface 1500 that includes an interactive element 1510 in the form of an interactive game. As will be understood by one skilled in the art, a user playing the interactive game on the user device 120 may provide user inputs (i.e., via touch screen or other input device) to interact and otherwise play the game. In various aspects, the Facial Interface Interaction Module 1400 may enable a user, through facial movement to provide specific input to the interactive game. Similar to recording a facial movement session, the system may track the user's facial movements to identify particular movements, and provide particular system inputs to the interactive game in response to identifying those movements. For example, a user playing PacMan® may provide touch-screen or other input to move the character around the screen, while consuming the pellets (and/or Ghosts) in the game by performing a 'chomping' motion. As shown in this figure, the user interface 1500 may include a feed of the front-facing (or other) camera of the device so that a user can see themselves while they play. The user interface 1500 may further include a scoreboard that tracks, suing any suitable technique described herein, game statistics, user analytics, etc. In this way, the system may be configured to gamify a particular facial movement regimen, while enabling a user to utilize facial movements as an additional input device for the user device 120.

For illustrative purposes, the Facial Interface Interaction Module 1400 described with reference to implementations described above with respect to one or more examples described herein. Other implementations, however, are possible. In some aspects, the steps in FIG. 14 may be implemented in program code that is executed by one or more computing devices such as the facial image processing and analysis computing system 100, the user device 120, or other system in FIG. 1. In some aspects, one or more operations shown in FIG. 14 may be omitted or performed in a different order. Similarly, additional operations not shown in FIG. 14 may be performed.

Custom Interface Generation Module

Figure 16:
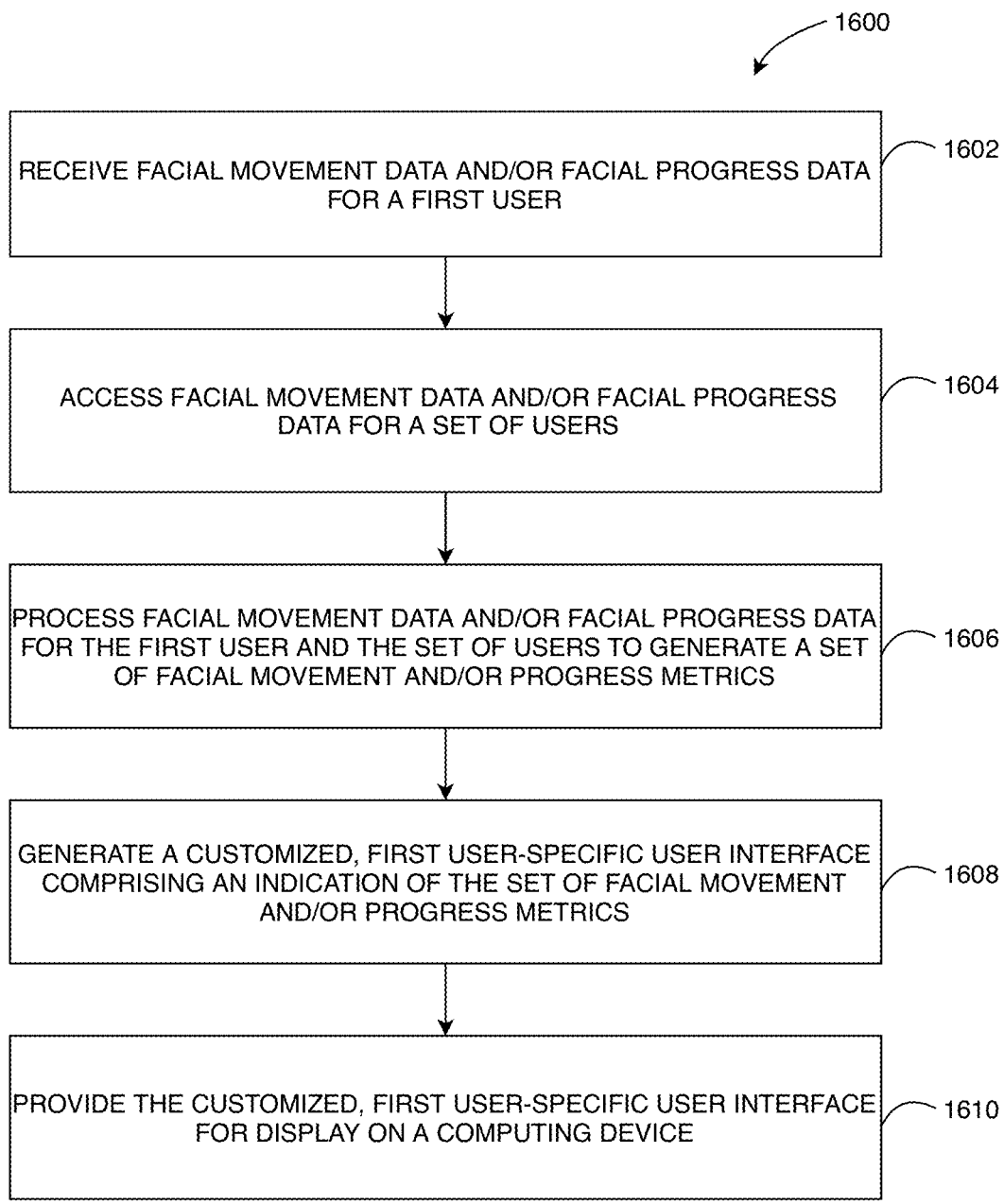
FIG. 16 depicts an example of a process for generating a customized user interface in accordance with various aspects of the present disclosure.

Turning now to FIG. 16, additional details are provided regarding a Custom Interface Generation Module 1600. For instance, the flow diagram shown in FIG. 16 may correspond to operations executed by computing hardware found in facial image processing and analysis computing system 100 as it executes the Custom Interface Generation Module 1600.

At operation 1602, the Custom Interface Generation Module 1600 receives facial movement data and/or facial progress data for a first user. The system may receive such data using any suitable technique described herein.

At operation 1604, the Custom Interface Generation Module 1600 accesses facial movement data and/or facial progress data for a set of users. In some aspects, the system may provide functionality to a plurality of users for the purposes of analyzing facial imaging data, tracking facial exercises, determining treatment and exercise plans, etc. In some aspects, the system may collect data from each of the plurality of users of the system.

At operation 1606, the Custom Interface Generation Module 1600 processes the facial movement data and/or facial progress data for the first user and the set of users to generate a set of facial movement and/or progress metrics.

The Custom Interface Generation Module 1600, at operation 1608, generates a customized, first user-specific user interface comprising an indication of the set of facial movement and/or progress metrics. In this way, the system may provide a platform via which a user can track their progress against and interact with other system users. The system may, for example, enable users to challenge others to particular exercises (e.g., perform a number of repetitions in a particular amount of time, burn a particular number of calories, establish a daily exercise streak, etc.).

At operation 1610, the Custom Interface Generation Module 1600 provides the user interface for display on a computing device (e.g., the user device 120).

For illustrative purposes, the Custom Interface Generation Module 1600 described with reference to implementations described above with respect to one or more examples described herein. Other implementations, however, are possible. In some aspects, the steps in FIG. 16 may be implemented in program code that is executed by one or more computing devices such as the facial image processing and analysis computing system 100, the user device 120, or other system in FIG. 1. In some aspects, one or more operations shown in FIG. 16 may be omitted or performed in a different order. Similarly, additional operations not shown in FIG. 16 may be performed.

Example Technical Platforms

Aspects of the present disclosure may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query, or search language, and/or a report writing language. In one or more example aspects, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established, or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In some aspects, a non-volatile computer-readable storage medium may include a floppy disk, flexible disk, hard disk, solid-state storage (SSS) (e.g., a solid-state drive (SSD), solid state card (SSC), solid state module (SSM)), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In some aspects, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where various aspects are described to use a computer-readable storage medium, other types of computer-readable storage media may be substituted for or used in addition to the computer-readable storage media described above.

Various aspects of the present disclosure may also be implemented as methods, apparatuses, systems, computing devices, computing entities, and/or the like. As such, various aspects of the present disclosure may take the form of a data structure, apparatus, system, computing device, computing entity, and/or the like executing instructions stored on a computer-readable storage medium to perform certain steps or operations. Thus, various aspects of the present disclosure also may take the form of entirely hardware, entirely computer program product, and/or a combination of computer program product and hardware performing certain steps or operations.

Various aspects of the present disclosure are described below with reference to block diagrams and flowchart illustrations. Thus, each block of the block diagrams and flowchart illustrations may be implemented in the form of a computer program product, an entirely hardware aspect, a combination of hardware and computer program products, and/or apparatuses, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some examples of aspects, retrieval, loading, and/or execution may be performed in parallel such that multiple instructions are retrieved, loaded, and/or executed together. Thus, such aspects can produce specially configured machines performing the steps or operations specified in the block diagrams and flowchart illustrations. Accordingly, the block diagrams and flowchart illustrations support various combinations of aspects for performing the specified instructions, operations, or steps.

Example System Architecture

Figure 17:
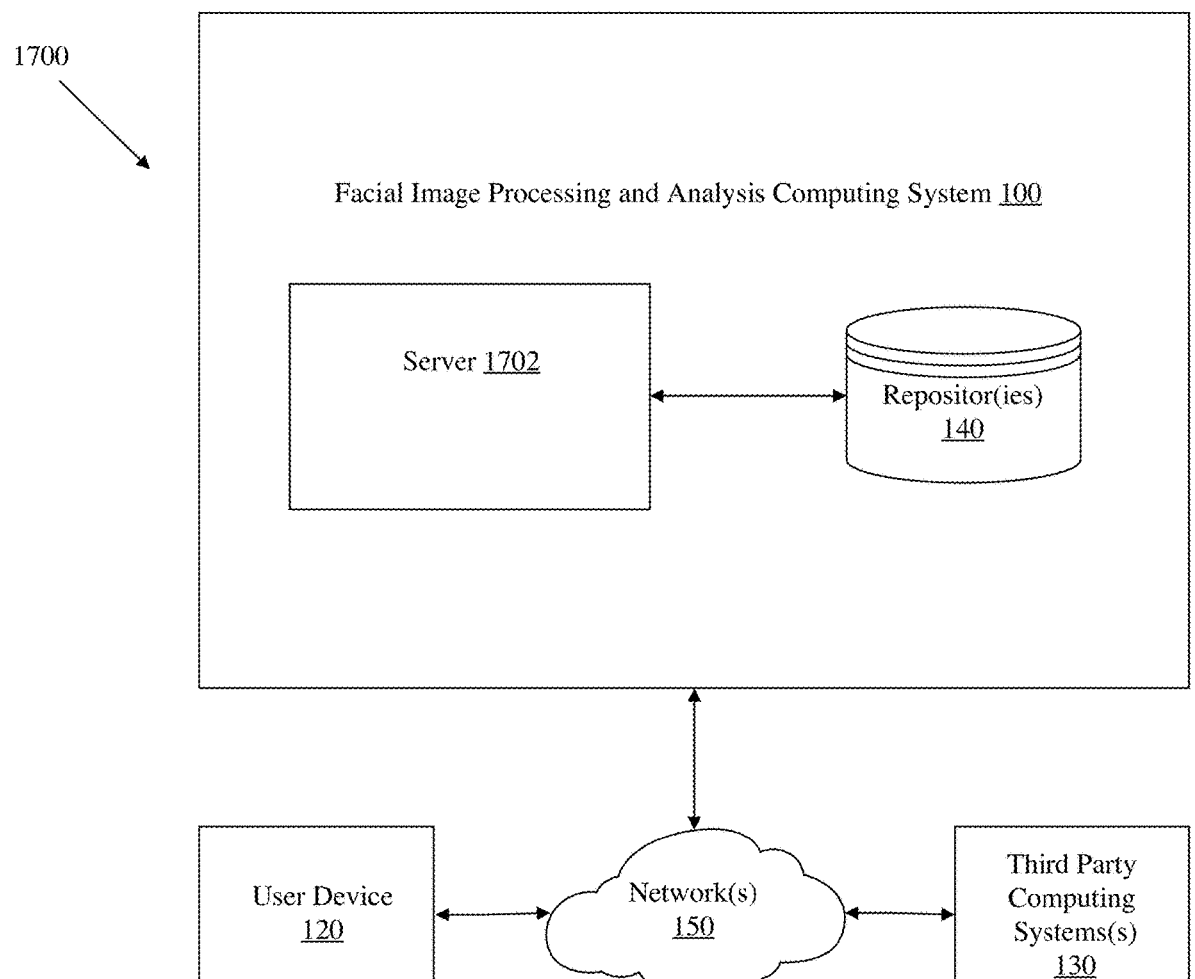
FIG. 17 depicts an example of a system architecture that may be used in accordance with various aspects of the present disclosure.

FIG. 17 is a block diagram of an example of a system architecture 1700 that can be for facial imaging data analysis platforms as described herein. As may be understood from FIG. 17, the system architecture 1700 in some aspects may include a facial image processing and analysis computing system 100 that comprises one or more servers 1702 and a data repository 140. The data repository 140 may be made up of computing components such as servers, routers, data storage, networks, and/or the like that are used on the facial image processing and analysis computing system 100 to store and manage user data, facial imaging data, exercise plan data and other data described herein.

As previously noted, the facial image processing and analysis computing system 100 may provide image analysis services that are available over one or more networks 150. Here, a user may access the service via a user device 120. For example, the facial image processing and analysis computing system 100 may provide the service through a website that is accessible to the user device 120 the one or more networks 150.

According, the server(s) 1702 may execute the various system modules as described herein. Further, according to particular aspects, the server(s) 1702 may provide one or more graphical user interfaces (e.g., one or more webpages, webform, and/or the like through the website) through which users can interact with the facial image processing and analysis computing system 100. Furthermore, the server(s) 1702 may provide one or more interfaces that allow the facial image processing and analysis computing system 100 to communicate with third-party computing system(s) 130 such as one or more suitable application programming interfaces (APIs), direct connections, and/or the like.

Example Computing Hardware

Figure 18:
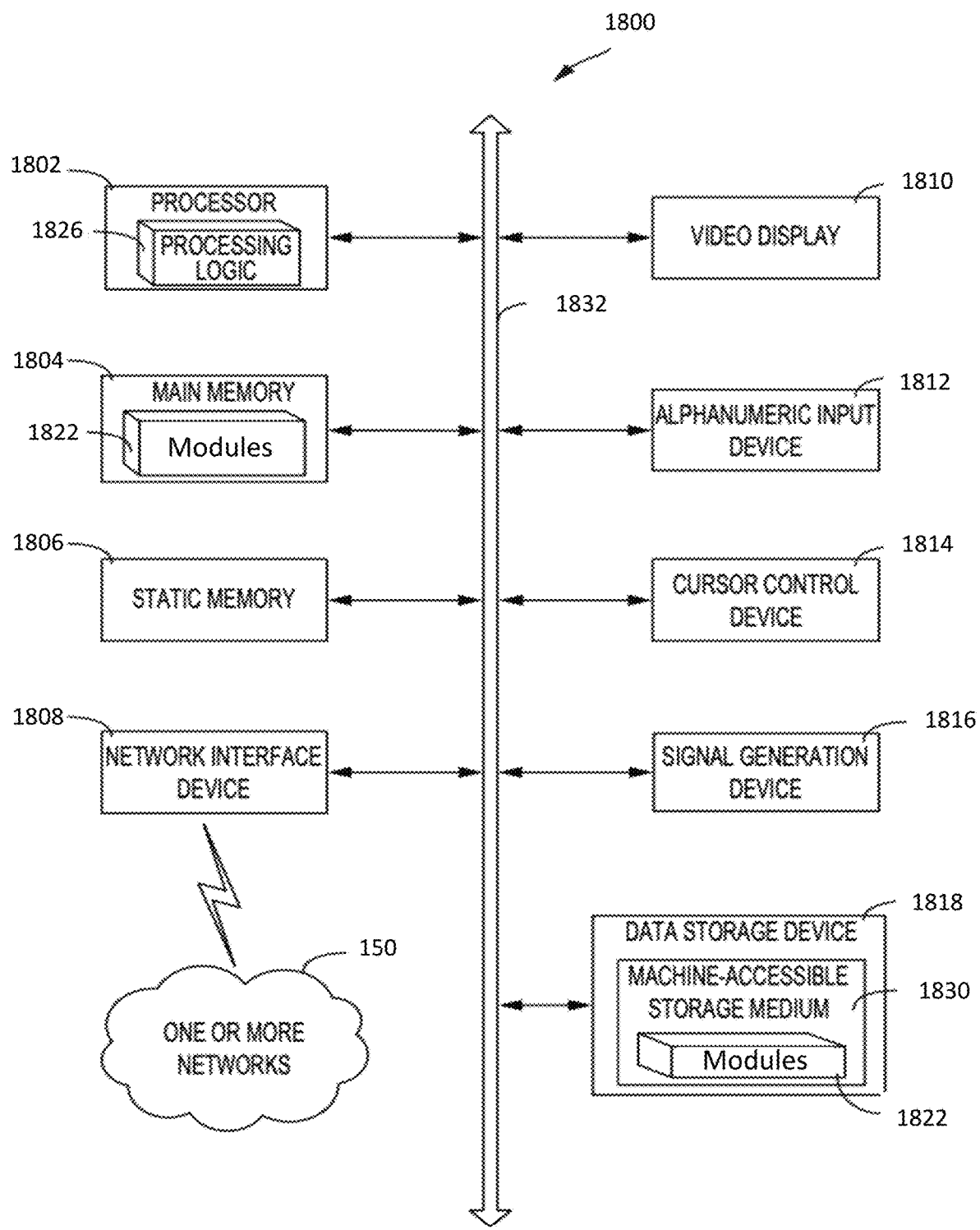
FIG. 18 depicts an example of a computing entity that may be used in accordance with various aspects of the present disclosure.

FIG. 18 illustrates a diagrammatic representation of a computing hardware device 1800 that may be used in accordance with various aspects. For example, the hardware device 1800 may be computing hardware such as a server 1802 as described in FIG. 18. According to particular aspects, the hardware device 1800 may be connected (e.g., networked) to one or more other computing entities, storage devices, and/or the like via one or more networks such as, for example, a LAN, an intranet, an extranet, and/or the Internet. As noted above, the hardware device 1800 may operate in the capacity of a server and/or a client device in a client-server network environment, or as a peer computing device in a peer-to-peer (or distributed) network environment. In some aspects, the hardware device 1800 may be a personal computer (PC), a tablet PC, a set-top box (STB), a Personal Digital Assistant (PDA), a mobile device (smartphone), a web appliance, a server, a network router, a switch or bridge, or any other device capable of executing a set of instructions (sequential or otherwise) that specify actions to be taken by that device. Further, while only a single hardware device 1800 is illustrated, the term "hardware device," "computing hardware," and/or the like shall also be taken to include any collection of computing entities that individually or jointly execute a set (or multiple sets) of instructions to perform any one or more of the methodologies discussed herein.

A hardware device 1800 includes a processor 1802, a main memory 1804 (e.g., read-only memory (ROM), flash memory, dynamic random-access memory (DRAM) such as synchronous DRAM (SDRAM), Rambus DRAM (RDRAM), and/or the like), a static memory 1806 (e.g., flash memory, static random-access memory (SRAM), and/or the like), and a data storage device 1818, that communicate with each other via a bus 1832.

The processor 1802 may represent one or more general-purpose processing devices such as a microprocessor, a central processing unit, and/or the like. According to some aspects, the processor 802 may be a complex instruction set computing (CISC) microprocessor, reduced instruction set computing (RISC) microprocessor, very long instruction word (VLIW) microprocessor, a processor implementing other instruction sets, processors implementing a combination of instruction sets, and/or the like. According to some aspects, the processor 1802 may be one or more special-purpose processing devices such as an application specific integrated circuit (ASIC), a field programmable gate array (FPGA), a digital signal processor (DSP), network processor, and/or the like. The processor 1802 can execute processing logic 1826 for performing various operations and/or steps described herein.

The hardware device 1800 may further include a network interface device 1808, as well as a video display unit 1810 (e.g., a liquid crystal display (LCD), a cathode ray tube (CRT), and/or the like), an alphanumeric input device 1812 (e.g., a keyboard), a cursor control device 1814 (e.g., a mouse, a trackpad), and/or a signal generation device 1816 (e.g., a speaker). The hardware device 800 may further include a data storage device 1818. The data storage device 1818 may include a non-transitory computer-readable storage medium 1830 (also known as a non-transitory computer-readable storage medium or a non-transitory computer-readable medium) on which is stored one or more modules 1822 (e.g., sets of software instructions) embodying any one or more of the methodologies or functions described herein. For instance, according to particular aspects, the modules 1822 include the Facial Scanning and Analysis Module 200, the Facial Movement Tracking Module 500, the Facial Modification Progress Tracking Module 800, the Facial Exercise Customization Module 1100, the Facial Exercise Model Training Module 1200, the Facial Movement Tracking Model Training Module 1300, The Facial Movement Interface Interaction Module 1400, and the Custom Interface Generation Module 1600 as described herein. The one or more modules 1822 may also reside, completely or at least partially, within main memory 804 and/or within the processor 1802 during execution thereof by the hardware device 1800—main memory 1804 and processor 1802 also constituting computer-accessible storage media. The one or more modules 1822 may further be transmitted or received over a network 150 via the network interface device 1808.

While the computer-readable storage medium1 1830 is shown to be a single medium, the terms "computer-readable storage medium" and "machine-accessible storage medium" should be understood to include a single medium or multiple media (e.g., a centralized or distributed database, and/or associated caches and servers) that store the one or more sets of instructions. The term "computer-readable storage medium" should also be understood to include any medium that is capable of storing, encoding, and/or carrying a set of instructions for execution by the hardware device 800 and that causes the hardware device 1800 to perform any one or more of the methodologies of the present disclosure. The term "computer-readable storage medium" should accordingly be understood to include, but not be limited to, solid-state memories, optical and magnetic media, and/or the like.

System Operation

The logical operations described herein may be implemented (1) as a sequence of computer implemented acts or one or more program modules running on a computing system and/or (2) as interconnected machine logic circuits or circuit modules within the computing system. The implementation is a matter of choice dependent on the performance and other requirements of the computing system. Accordingly, the logical operations described herein are referred to variously as states, operations, steps, structural devices, acts, or modules. These states, operations, steps, structural devices, acts, and modules may be implemented in software, in firmware, in special purpose digital logic, and any combination thereof. Greater or fewer operations may be performed than shown in the figures and described herein. These operations also may be performed in a different order than those described herein.

CONCLUSION

While this specification contains many specific aspect details, these should not be construed as limitations on the scope of any invention or of what may be claimed, but rather as descriptions of features that may be specific to particular aspects of particular inventions. Certain features that are described in this specification in the context of separate aspects also may be implemented in combination in a single aspect. Conversely, various features that are described in the context of a single aspect also may be implemented in multiple aspects separately or in any suitable sub-combination. Moreover, although features may be described above as acting in certain combinations and even initially claimed as such, one or more features from a claimed combination may in some cases be excised from the combination, and the claimed combination may be a sub-combination or variation of a sub-combination.

Similarly, while operations are described in a particular order, this should not be understood as requiring that such operations be performed in the particular order described or in sequential order, or that all described operations be performed, to achieve desirable results. In certain circumstances, multitasking and parallel processing may be advantageous. Moreover, the separation of various components in the various aspects described above should not be understood as requiring such separation in all aspects, and the described program components (e.g., modules) and systems may be integrated together in a single software product or packaged into multiple software products.

Many modifications and other aspects of the disclosure will come to mind to one skilled in the art to which this disclosure pertains having the benefit of the teachings presented in the foregoing descriptions and the associated drawings. Therefore, it is to be understood that the disclosure is not to be limited to the specific aspects disclosed and that modifications and other aspects are intended to be included within the scope of the appended claims. Although specific terms are employed herein, they are used in a generic and descriptive sense only and not for the purposes of limitation.

What is claimed is:

1. A computer-implemented data processing method of generating user-specific analytics from facial imaging data comprising:
   receiving, by computing hardware, facial imaging data of a user, the facial imaging data including imaging data of at least a portion of a jaw and facial structure of the user;
   accessing, by the computing hardware, user attribute data for the user, the user attribute data defining one or more of:
      an age of the user;
      a gender of the user;
      a weight of the user;
      a face shape of the user; or
      a relative position of one or more user facial features;
   processing, by the computing hardware, the facial imaging data and the user attribute data using at least one of a rules-based model or a machine learning model to generate a user-specific first data analytic for the user, the first data analytic comprising at least one of:
      a number of calories burned by the user during a time period demonstrated by the facial imaging data; or
      a number of repetitions of a particular movement performed by at least one of the at least a portion of the jaw or the facial structure of the user; and
   generating, by the computing hardware, a graphical user interface comprising an indication of the first data analytic;
   providing, by the computing hardware, the graphical user interface for display on a computing device;
   analyzing, by the computing hardware, the facial imaging data;
   determining, based on analysis of the facial imaging data, that the user has a jaw exercise apparatus in a mouth of the user;
   determining, by the computing hardware, a type of the jaw exercise device; and
   modifying, by the computing hardware, the first data analytic based at least in part on the type of the jaw exercise device.

2. The computer-implemented data processing method of claim 1, wherein:
the first data analytic comprises the number of repetitions of the particular movement; and
the method further comprises providing, by the computing hardware for each repetition of the repetitions of the particular movement, a particular input to the computing device.

3. A computer-implemented data processing method of generating user-specific analytics from facial imaging data comprising:
receiving, by computing hardware, facial imaging data of a user, the facial imaging data including imaging data of at least a portion of a jaw and facial structure of the user;
accessing, by the computing hardware, user attribute data for the user, the user attribute data defining one or more of:
an age of the user;
a gender of the user;
a weight of the user;
a face shape of the user; or
a relative position of one or more user facial features;
processing, by the computing hardware, the facial imaging data and the user attribute data using at least one of a rules-based model or a machine learning model to generate a user-specific first data analytic for the user, the first data analytic comprising at least one of:
a number of calories burned by the user during a time period demonstrated by the facial imaging data; or
a number of repetitions of a particular movement performed by at least one of the at least a portion of the jaw or the facial structure of the user; and
generating, by the computing hardware, a graphical user interface comprising an indication of the first data analytic;
providing, by the computing hardware, the graphical user interface for display on a computing device;
analyzing, by the computing hardware, the facial imaging data to identify at least one facial defect;
receiving, by the computing hardware, second facial imaging data;
analyzing, by the computing hardware, the second facial imaging data to determine a change in the at least one facial defect;
processing, by the computing hardware, the facial imaging data, the at least one facial defect, and the change in the at least one facial defect to determine a correction progress of the at least one facial defect; and
providing, by the computing hardware, an indication of the correction progress of the at least one facial defect for display on a user interface.

4. The computer implemented data processing method of claim 3, further comprising:
processing, by the computing hardware, the facial imaging data, the user attribute data and the at least one facial defect using at least one of a rules-based model or a machine learning model to generate a user-specific defect correction plan; and
generating, by the user interface, a user interface comprising the user-specific defect correction plan.

5. The computer-implemented data processing method of claim 4, wherein the at least one of the rules-based model or the machine learning model were trained with historical facial progress data and facial movement data for each user in a set of users.

6. A system comprising:
a non-transitory computer-readable medium storing instructions; and
a processing device communicatively coupled to the non-transitory computer-readable medium, wherein the processing device is configured to execute the instructions and thereby perform operations comprising:
receiving facial imaging data of a user, the facial imaging data including imaging data of at least a portion of a jaw and facial structure of the user;
accessing user attribute data for the user, the user attribute data defining one or more of:
an age of the user;
a gender of the user;
a weight of the user;
a face shape of the user; or
a relative position of one or more user facial features;
processing the facial imaging data and the user attribute data using at least one of a rules-based model or a machine learning model to generate a user-specific first data analytic for the user, the first data analytic comprising at least one of:
a number of calories burned by the user during a time period demonstrated by the facial imaging data; or
a number of repetitions of a particular movement performed by at least one of the at least a portion of the jaw or the facial structure of the user;
generating a graphical user interface comprising an indication of the first data analytic;
providing the graphical user interface for display on a computing device;
analyzing the facial imaging data;
determining that the user has a jaw exercise apparatus in a mouth of the user;
determining a type of the jaw exercise device; and
modifying the first data analytic based at least in part on the type of the jaw exercise device.

7. The system of claim 6, wherein
the first data analytic comprises the number of repetitions of the particular movement; and
the operations further comprise providing, for each repetition of the repetitions of the particular movement, a particular input to the computing device.

8. A system comprising:
a non-transitory computer-readable medium storing instructions; and
a processing device communicatively coupled to the non-transitory computer-readable medium, wherein the processing device is configured to execute the instructions and thereby perform operations comprising:
receiving facial imaging data of a user, the facial imaging data including imaging data of at least a portion of a jaw and facial structure of the user;
accessing user attribute data for the user, the user attribute data defining one or more of:
an age of the user;
a gender of the user;
a weight of the user;
a face shape of the user; or
a relative position of one or more user facial features;
processing the facial imaging data and the user attribute data using at least one of a rules-based model or a machine learning model to generate a user-specific first data analytic for the user, the first data analytic comprising at least one of:

a number of calories burned by the user during a time period demonstrated by the facial imaging data; or a number of repetitions of a particular movement performed by at least one of the at least a portion of the jaw or the facial structure of the user;

generating a graphical user interface comprising an indication of the first data analytic;

providing the graphical user interface for display on a computing device;

analyzing the facial imaging data to identify at least one facial defect;

receiving second facial imaging data;

analyzing the second facial imaging data to determine a change in the at least one facial defect;

processing the facial imaging data, the at least one facial defect, and the change in the at least one facial defect to determine a correction progress of the at least one facial defect; and providing an indication of the correction progress of the at least one facial defect for display on a user interface.

9. The system of claim 8, the operations further comprising:

processing the facial imaging data, the user attribute data, and the at least one facial defect using at least one of a rules-based model or a machine learning model to generate a user-specific defect correction plan; and generating a user interface comprising the user-specific defect correction plan.

10. The system of claim 9, wherein the at least one of the rules-based model or the machine learning model were trained with historical facial progress data and facial movement data for each user in a set of users.

11. A system comprising:

a non-transitory computer-readable medium storing instructions; and a processing device communicatively coupled to the non-transitory computer-readable medium, wherein the processing device is configured to execute the instructions and thereby perform operations comprising:

receiving facial imaging data of a user, the facial imaging data including imaging data of at least a portion of a jaw and facial structure of the user;

accessing user attribute data for the user, the user attribute data defining one or more of:

an age of the user;

a gender of the user;

a weight of the user;

a face shape of the user; or a relative position of one or more user facial features;

processing the facial imaging data and the user attribute data using at least one of a rules-based model or a machine learning model to generate a user-specific first data analytic for the user, the first data analytic comprising at least one of:

a number of calories burned by the user during a time period demonstrated by the facial imaging data; or a number of repetitions of a particular movement performed by at least one of the at least a portion of the jaw or the facial structure of the user;

generating a graphical user interface comprising an indication of the first data analytic;

providing the graphical user interface for display on a computing device;

analyzing the facial imaging data to identify at least one facial defect;

processing the facial imaging data, the user attribute data, and the at least one facial defect using at least one of a rules-based model or a machine learning model to generate a user-specific defect correction plan; and generating a user interface comprising the user-specific defect correction plan.

12. A non-transitory computer-readable medium having program code that is stored thereon, the program code executable by one or more processing devices for performing operations comprising:

receiving facial imaging data of a user, the facial imaging data including imaging data of at least a portion of a jaw and facial structure of the user;

accessing user attribute data for the user, the user attribute data defining one or more of:

an age of the user;

a gender of the user;

a weight of the user;

a face shape of the user; or a relative position of one or more user facial features;

processing the facial imaging data and the user attribute data using at least one of a rules-based model or a machine learning model to generate a user-specific first data analytic for the user, the first data analytic comprising at least one of:

a number of calories burned by the user during a time period demonstrated by the facial imaging data; or a number of repetitions of a particular movement performed by at least one of the at least a portion of the jaw or the facial structure of the user;

generating a graphical user interface comprising an indication of the first data analytic;

providing the graphical user interface for display on a computing device;

analyzing the facial imaging data;

determining that the user has a jaw exercise apparatus in a mouth of the user;

determining a type of the jaw exercise device; and modifying the first data analytic based at least in part on the type of the jaw exercise device.

13. The non-transitory computer-readable medium of claim 12, wherein the first data analytic comprises the number of repetitions of the particular movement; and the operations further comprise providing, for each repetition of the repetitions of the particular movement, a particular input to the computing device.

14. A non-transitory computer-readable medium having program code that is stored thereon, the program code executable by one or more processing devices for performing operations comprising:

receiving facial imaging data of a user, the facial imaging data including imaging data of at least a portion of a jaw and facial structure of the user;

accessing user attribute data for the user, the user attribute data defining one or more of:

an age of the user;

a gender of the user;

a weight of the user;

a face shape of the user; or a relative position of one or more user facial features;

processing the facial imaging data and the user attribute data using at least one of a rules-based model or a machine learning model to generate a user-specific first data analytic for the user, the first data analytic comprising at least one of:

a number of calories burned by the user during a time period demonstrated by the facial imaging data; or a number of repetitions of a particular movement performed by at least one of the at least a portion of the jaw or the facial structure of the user;
generating a graphical user interface comprising an indication of the first data analytic;
providing the graphical user interface for display on a computing device;
analyzing the facial imaging data to identify at least one facial defect;
receiving second facial imaging data;
analyzing the second facial imaging data to determine a change in the at least one facial defect;
processing the facial imaging data, the at least one facial defect, and the change in the at least one facial defect to determine a correction progress of the at least one facial defect; and
providing an indication of the correction progress of the at least one facial defect for display on a user interface.

15. The non-transitory computer-readable medium of claim 14, the operations further comprising:
Processing the facial imaging data, the user attribute data, and the at least one facial defect using at least one of a rules-based model or a machine learning model to generate a user-specific defect correction plan; and
Generating a user interface comprising the user-specific defect correction plan.

16. The non-transitory computer-readable medium of claim 15, wherein the at least one of the rules-based model or the machine learning model were trained with historical facial progress data and facial movement data for each user in a set of users.

17. The non-transitory computer-readable medium of claim 15, the operations further comprising:
analyzing the facial imaging data to identify at least one facial defect;
processing the facial imaging data, the user attribute data, and the at least one facial defect using at least one of a rules-based model or a machine learning model to generate a user-specific defect correction plan; and
generating a user interface comprising the user-specific defect correction plan.

* * * * *